(12) United States Patent
Ozaki et al.

(10) Patent No.: US 8,414,848 B2
(45) Date of Patent: Apr. 9, 2013

(54) SUBSTRATE INCLUDING CHANNEL PART HAVING CHAMBER, AND MULTISTAGE LIQUID FEED DEVICE COMPRISING THE SAME

(75) Inventors: Nobuhiko Ozaki, Kanagawa (JP); Airi Takagi, Kanagawa (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/598,146

(22) PCT Filed: Apr. 23, 2008

(86) PCT No.: PCT/JP2008/001062
§ 371 (c)(1),
(2), (4) Date: Oct. 29, 2009

(87) PCT Pub. No.: WO2008/139697
PCT Pub. Date: Nov. 20, 2008

(65) Prior Publication Data
US 2010/0132820 A1    Jun. 3, 2010

(30) Foreign Application Priority Data
May 10, 2007    (JP) .................................. 2007-125908

(51) Int. Cl.
*B01L 3/00* (2006.01)
*F04B 19/00* (2006.01)
*G01N 35/00* (2006.01)
*G01N 1/10* (2006.01)

(52) U.S. Cl. .......... 422/503; 422/502; 422/506; 436/43; 436/45; 436/180

(58) Field of Classification Search .................. 422/503, 422/506
See application file for complete search history.

(56) References Cited

U.S. PATENT DOCUMENTS

| | | | |
|---|---|---|---|
| 7,104,517 B1 | 9/2006 | Derand et al. | |
| 2002/0150512 A1* | 10/2002 | Kellogg et al. | 422/103 |
| 2007/0003437 A1* | 1/2007 | Ozaki et al. | 422/64 |
| 2009/0087345 A1 | 4/2009 | Yamamoto | |

FOREIGN PATENT DOCUMENTS

| | | |
|---|---|---|
| JP | 2-232563 | 9/1990 |
| JP | 2000-065778 | 3/2000 |
| JP | 2001-503854 | 3/2001 |
| JP | 2002-503331 | 1/2002 |

(Continued)

OTHER PUBLICATIONS

Micro Total Analysis Systems 2000, pp. 311-314.

(Continued)

*Primary Examiner* — Jill Warden
*Assistant Examiner* — Charles D Hammond
(74) *Attorney, Agent, or Firm* — Greenblum & Bernstein, P.L.C.

(57) ABSTRACT

A substrate including a channel part having a chamber in which a liquid can be fed stepwise from a chamber to another chamber at the channel part formed in the substrate, depending on the rotational speed of the substrate. A first chamber, a second chamber, a third chamber, and a channel interconnecting them are formed at the channel part formed in the substrate. Furthermore, the width and/or the depth of the first chamber is set smaller than the width and/or the depth of the second chamber. Consequently, the volume of solution subjected to centrifugal force in the first chamber is larger than the volume of solution subjected to centrifugal force in the second chamber.

16 Claims, 27 Drawing Sheets

FOREIGN PATENT DOCUMENTS

| | | |
|---|---|---|
| JP | 3356784 | 10/2002 |
| JP | 2003-503716 | 1/2003 |
| JP | 3469585 | 9/2003 |
| WO | 97/21090 | 6/1997 |
| WO | 98/07019 | 2/1998 |
| WO | 98/38510 | 9/1998 |
| WO | 98/53311 | 11/1998 |

OTHER PUBLICATIONS

English language Abstract of WO 98/07019, corresponding to JP 2001-503854.

English language Abstract of WO 01/02737, corresponding to JP 2003-503716.

English language Abstract of WO 97/21090, corresponding to JP 2002-503331.

English language Abstract of WO 98/38510, corresponding to JP 3356784.

English language Abstract of WO 98/53311, corresponding to JP 3469585.

International Search Report issued with respect to PCT/JP2008/001062, mailed Jun. 10, 2008.

* cited by examiner $rpm_1 \leq$ ROTATION SPEED $< rpm_2$

SUBSTRATE INCLUDING CHANNEL PART HAVING CHAMBER, AND MULTISTAGE LIQUID FEED DEVICE COMPRISING THE SAME

TECHNICAL FIELD

The present invention relates to a substrate having a flow path part including chambers and a liquid transfer apparatus including the substrate. Particularly, the present invention relates to a multistage liquid transfer apparatus for transferring liquid stepwise through chambers that the flow path parts of a substrate have, by controlling the flow of a small amount of solution.

BACKGROUND ART

In recent years, various health check chips have been developed. Most of these health check chips are card devices called "μ-TAS" (Micro Total Analysis System), which have miniature flow path parts. A miniaturized flow path is very useful in that the required amount of a sample to extract from a living organism is small. Further, when entire apparatus including the health check chip is made small by miniaturizing the flow path, the apparatus is applicable for use in POCT (Point of Care Test) that allows diagnosis in doctor's offices and households, not only in relatively large-scale hospitals.

In cases where a large amount of fluid flows, a pump is generally used as liquid transferring means. However, in a miniature flow path in which only a very small amount of fluid flows, it is not possible to disregard the influence of the dead volume generated in tubes connected with the pump. Therefore, a pump is generally not suitable for the liquid transfer means of for chips used in POCT.

Using centrifugal force for the source drive is one method of liquid transfer suitable for use in POCT (for example, Patent Documents 1 to 5). A method of liquid transfer using centrifugal force offers an advantage of not generating a dead volume and performing many processes at the same time in parallel.

For example, the substrate disclosed in Non-Patent Document 1 has a plurality of microchambers and micro-flow paths. In the substrate, the widths of the micro-flow paths connecting between the microchambers are adjusted each other. To be more specific, in a range between about 10 μm and 100 μm, micro-flow paths that are more distant from the center of rotation have a narrower width. By this means, a micro-flow path that is more distant from the axis of rotation generates greater capillary force. Liquid in the miniature chambers, the liquid transfer of which is prevented by the capillary force produced in the micro-flow paths, is transferred to the neighboring microchambers in the direction of centrifugal force by the centrifugal force produced by the rotation of the substrate. The centrifugal force required to transfer liquid in a microchamber matches the capillary force produced in a micro-flow path. As described above, a micro-flow path is designed to produce greater capillary force when the micro-flow path is placed more distant from the axis of rotation. Therefore, without increasing the speed of rotation, it is not possible to transfer liquid from one microchamber to a neighboring microchamber in the direction of centrifugal force. That results in realizing stepwise liquid transfer.

Patent Document 1: Japanese Patent Application Laid-Open No. 2000-065778

Patent Document 2: Japanese Translation of a PCT Application Laid-Open No. 2001-503854

Patent Document 3: Japanese Translation of a PCT Application Laid-Open No. 2002-503331

Patent Document 4: Japanese Patent No. 3356784

Patent Document 5: Japanese Patent No. 3469585

Non-Patent Document 1: Micro Total Analysis Systems 2000, pp. 311-314

DISCLOSURE OF INVENTION

Problems to be Solved by the Invention

However, in the substrate for transferring liquid using multiple chambers disclosed in Patent Document 1, there are two factors to limit the width of flow paths.

The first limiting factor is that the width of the flow paths varying according to positions of chambers (i.e. the distances from the center of rotation) is made equal to or less than the depth of the flow path. The present inventors have attempted multistage liquid transfer using a substrate including flat flow paths that have a greater width than the depth, despite the first limiting factor. The number of stages of chambers is three, the flow path width on the inner periphery side was 750 μm, the flow path width on the outer periphery side was 300 μm and the flow path depth was 15 μm. However, it was not possible to carry out multistage liquid transfer. To be more specific, upon making the substrate rotate at the first rotation speed, liquid in the innermost chamber did not stay in the chamber that was connected next, and was transferred to the outermost chamber all at once.

One possible reason that the desired liquid transfer operation was not possible is that the widths of the flow paths (750 μm and 300 μm) were made greater than the depth of the flow paths (15 μm). The pressure that is produced on the cross-section of flow path by capillary force is in proportion to the perimeter of the cross-section and in reverse proportion to the cross-sectional area of the flow path. Therefore, to significantly increase the capillary force that is produced on the cross-section of the flow path, the increase in the perimeter needs to be greater than the increase of the cross-sectional area. For that reason, in cross-sectional area of a flow path configured with the width and the depth, the shortest dimension needs to be made small.

The second limiting factor is that a micro-flow path that is more distant from the axis of rotation has a narrower width. The flow path having a width or depth between about 10 μm and 100 μm is generally made using photolithography technology. Although the widths of flow paths can be adjusted by changing the line widths of the photo-masks, there is a limit for making the flow paths narrow. It is necessary to make the narrower width of flow paths as the number of stages of chambers increases. However, regarding a flow path having the depth of 100 μm, it is not possible to make the width about 1 μm or less, that is, to make the aspect ratio 100 or more with today's technologies. Further, the depth of flow paths is determined depending on the etching depth, and therefore it is difficult to form regional parts corresponding to flow paths having different depths.

As described above, the process of making a substrate that realizes stepwise liquid transfer by adjusting the cross-sectional area of micro-flow paths, involves a heavy load. Furthermore, there are cases where the substrate that realizes multistage liquid transfer cannot be made.

Further, in Non-Patent Document 1, experiments are conducted using an electrolyte aqueous solution as a liquid transfer reagent. A biological sample (e.g. human blood) is more viscous than an electrolyte aqueous solution, to have difficulty flowing in micro-flow paths. Further, a solution containing a variety of proteins allows the adhesive proteins to adhere to the interior walls of micro-flow paths, and therefore the adherent proteins may cause micro-flow paths to be blocked.

It is therefore an object of the present invention to provide a substrate in which liquid is transferred stepwise through microchambers according to the rotation speed of the substrate, without changing on a per micro-flow path basis the cross-section of micro flow paths communicating between the michrochambers. Further, it is another object of the present invention to make a substrate in light load processes.

Further, it is another object of the present invention to provide a substrate that ensures smooth flow of biological samples without adding treatment for preventing adhesion to micro-flow paths.

Furthermore, it is another object of the present invention to provide a method of transferring liquid stepwise through microchambers using the substrate of the present invention.

Means for Solving the Problem

The first aspect of the present invention relates to the following substrate that enables a very small amount of solution to be transferred stepwise.

A substrate that is rotatable around an axis of rotation and that has a flow path part formed inside the substrate, wherein: the flow path part comprises:
(A) a first chamber that has an injection inlet;
(B) a second chamber that is placed in a position more distant from the axis of rotation than the first chamber;
(C) a third chamber that is connected with outer atmosphere of the substrate via an air opening and that is placed in a position more distant from the axis of rotation than the second chamber;
(D) a first flow path that communicates the first chamber and the second chamber, that has a first flow path end part connected with the first chamber and is placed in a position more distant from the axis of rotation than the injection inlet, and that has a second flow path end part connected with the second chamber;
(E) a second flow path that communicates the second chamber and the third chamber, that has a third flow path end part connected with the second chamber and is not placed on a straight line connecting the axis of rotation and the second flow path end part, and that has a fourth flow path end part connected with the third chamber and placed in a position more distant from the axis of rotation than the second flow path end part and the air opening; a very small amount of a solution is transferred stepwise in order of the first chamber, second chamber and third chamber;
a cross-sectional area of a bottom surface of the first chamber near the first flow path end part is larger than the cross-sectional area of the first flow path near the first flow path end part; and
an imaginary length of the first chamber is longer than an imaginary length of the second chamber, the imaginary length of the first chamber being the distance from the first flow path end part to a surface of the solution along the centripetal direction toward the axis of rotation, when a certain amount of solution is accommodated in the first chamber and the substrate rotates about the axis of rotation, the imaginary length of the second chamber being the distance from the third flow path end part to a surface of the solution along the centripetal direction toward the axis of rotation, when the certain amount of solution is accommodated in the second chamber and the substrate rotates about the axis of rotation.

A second aspect of the present invention relates to the following multistage liquid transfer method that can transfer a very small amount of solution stepwise.

A multistage liquid transfer method includes steps of: preparing the substrate of the present invention, in which a solution is accommodated in a first chamber; rotating the substrate around an axis of rotation at a first rotation speed $rpm_1$; and rotating the substrate at a second rotation speed $rpm_2$ higher than the first rotation speed $rpm_1$.

A third aspect of the present invention relates to the following multistage liquid transfer apparatus that can transfer a very small amount of solution stepwise.

A multistage liquid transfer apparatus includes: the substrate of the present invention; and a rotation drive part that rotates the substrate around an axis of rotation.

Advantageous Effects of Invention

With the substrate of the present invention, it is possible to transfer liquid through chambers in flow path parts according to the rotation speed of the substrate. This stepwise liquid transfer is realized by controlling the "imaginary chamber length" so that the shapes of chambers in a flow path part are adjusted according to the distance from the axis of rotation. Consequently, the cross section and shape of flow paths that connect between chambers do not need to vary on a per flow path basis, so that the flow paths can be designed to be the same width or depth.

With the substrate of the present invention, the volume of solution that produces on centrifugal force working on flow path end parts of chambers is made lower in chambers on more outer periphery side. Centrifugal force inherently increases according to the distance from the axis of rotation. With the substrate of the present invention, the speed of rotation that generates centrifugal force exceeding the capillary force is set higher in chambers on more outer periphery side. As a result, it is possible to transfer liquid stepwise through chambers according to the rotation speed of the substrate.

Further, by adjusting the shape of micro-flow paths (i.e. the cross-sectional area near the end of micro-flow paths), it is possible to more reliably transfer biological samples stepwise between chambers. The substrate of the present invention is very practical, so that it is possible to give the substrate various functions. Further, stepwise liquid transfer is realized even when the volume of solution to transfer is very little. Further, the substrate of the present invention is easily produced, and the production process involves a light load.

BEST MODE FOR CARRYING OUT THE INVENTION

Figure 1:
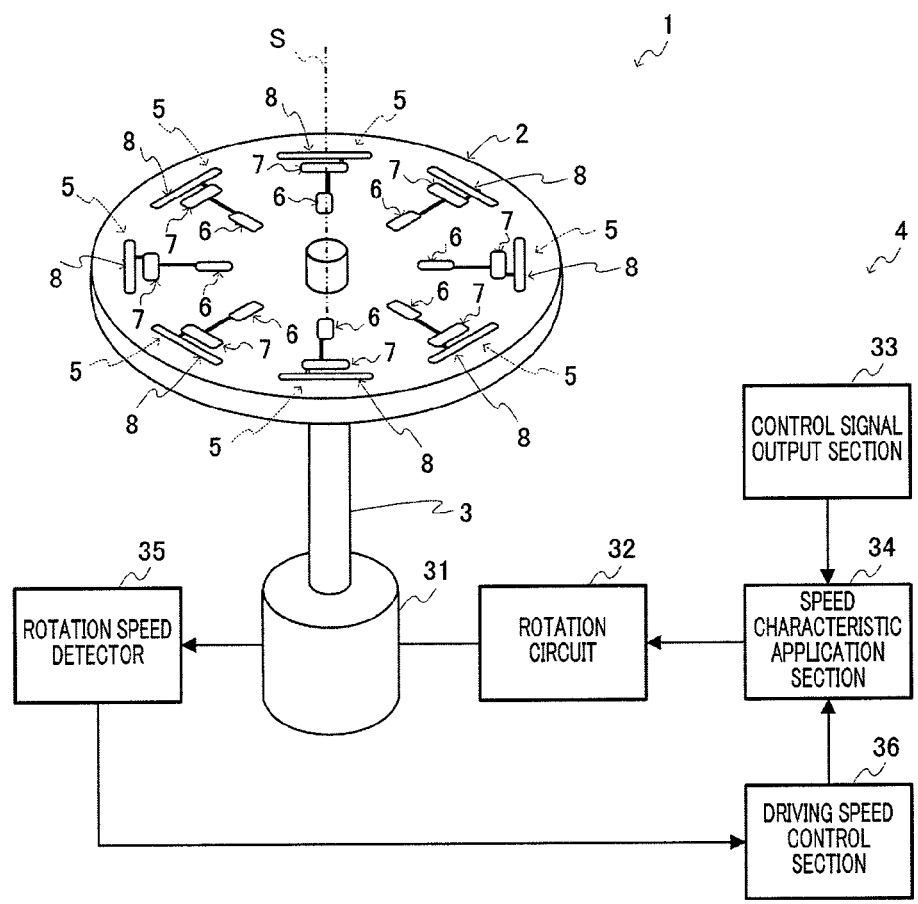
FIG. 1 is a schematic diagram showing the liquid transfer apparatus according to Embodiment 1.

1. The Substrate of the Present Invention

The substrate of the present invention has flow path parts. One or more flow path parts are formed inside the substrate. Each flow path part has two or more chambers and flow paths that communicate the chambers.

By rotating the substrate of the present invention around the axis of rotation, it is possible to stepwise transfer liquid supplied in the flow path parts to chambers. The direction of rotation of the substrate is defined as being as perpendicular to an imaginary line intersecting with the axis of rotation at right angles and as sharing the same plane with the imaginary line. For example, when the substrate is fixed to the rotating shaft, the tangential directions perpendicular to the radial directions of the rotating shaft are the directions of rotation. The directions of rotation can be clockwise or counterclockwise with respect to the axis of rotation in a plan view.

The outer shape of the substrate is not limited to a circle, and may be a cube, a rectangular parallelepiped, polygon such as pentagon, star shape and so on.

The flow path parts have the first chamber, a second chamber and a third chamber. All chambers are formed inside the substrate. The outer shapes of the first chamber, second chamber, and third chambers are not limited, and any shapes are set, such as substantially rectangular shapes and pillar shapes.

The first chamber has an injection inlet. Solution is supplied through the injection inlet. It is preferable that the first chamber is spatially closed except for the injection inlet. The injection inlet is placed in arbitrary positions on the first chamber. The second chamber is placed in a position more distant from the axis of rotation than the first chamber. The second chamber can be spatially closed. The third chamber has an air opening, and is connected with outer atmosphere of the substrate via the air opening. The third chamber is placed more distant from the axis of rotation than the second chamber. Consequently, the first chamber, second chamber and third chamber are placed in order from the axis of rotation.

The second chamber may have an air opening, and may be spatially closed except for the air opening. Assuming that the solution is transferred from the first chamber to the second chamber that does not have an air opening, air in the second chamber is exhausted through an air opening that is provided in the third chamber connected via the second flow path. However, if the second chamber does not have an air opening and is filled with a certain amount of solution, the inlet end part of the second flow path (the third flow path end part) connected with the second chamber is blocked with the solution, and therefore, the air has no way of escape. For that reason, the flow of the solution into the second chamber may stop. Consequently, by providing an air opening in the second chamber, it is possible to transfer liquid to the second chamber reliably.

The cross-sectional shape of the injection inlet or air opening formed in each chamber, may be a circle, oval, polygon or other shapes. The air opening may be made from a material that is air-transmissible and that is not solution-transmissible. In this case, leakage of solution upon rotating the substrate needs not to be taken into consideration, so that it is possible to make the air opening comparatively a large area.

Flow path parts also have the first flow path that communicates the first chamber and the second chamber, and a second flow path that communicates the second chamber and a third chamber.

The first flow path has the first flow path end part connected with the first chamber. The first flow path end part is placed in a position more distant from the axis of rotation than the injection inlet. The first flow path also has the second flow path end part connected with the second chamber. The second flow path end part is preferably placed in a position near the axis of rotation side in the second chamber.

The second flow path has a third flow path end part connected with the second chamber. The third flow path end part is preferably placed in a position distant from the axis of rotation in the second chamber. The third flow path end part is not on the straight line that connects the center of rotation and the second flow path end part. Further, the second flow path has a fourth flow path end part connected with the third chamber.

The third flow path end part of the second flow path (i.e. the part connecting with the second chamber) can have the same or a larger cross-sectional area than the first flow path end part of the first flow path (i.e. the part connecting with the first chamber). With a conventional substrate, a flow path that is more distant from the center of rotation has a smaller cross-sectional area to increase capillary force. However, with the substrate of the present invention, by changing the shape of chambers adequately, the centrifugal force that a solution in the chambers receives is adjusted (described later). And therefore, a flow path more distant from the center of rotation does not need to have smaller cross-sectional area, and has a constant cross-sectional area or larger cross-sectional area. By adjusting cross-sectional areas of micro-flow paths, the manufacturing process generally increases a load, so that it is preferable to make the micro-flow paths the same cross-sectional area. "The cross-sectional area of flow path end part" refers to the minimum cross-sectional area when a cross-sectional area near the flow path end part is not constant.

Flow path parts in the substrate of the present invention have a feature that "the first imaginary chamber length" is longer than "a second imaginary chamber length." "The first imaginary chamber length" refers to the distance from the first flow path end part to the surface of solution along the direction toward the center of rotation of the substrate (i.e. the centripetal direction), when a certain amount of solution (also referred to as the "imaginary chamber volume") is accommodated in the first chamber and the substrate is rotated about the axis of rotation to form the surface of solution. Similarly, "the second imaginary chamber length" refers to the distance from the third flow path end part to the surface of solution along the direction toward the center of rotation of the substrate (i.e. the centripetal direction) when the certain amount of solution is accommodated in the second chamber and the substrate is rotated about the axis of rotation to form the surface of solution. That is, when the same amount of solution is accommodated in the first chamber and the second chamber, the first imaginary chamber length becomes longer than the second imaginary chamber length.

Solution accommodated in chambers tries to flow in flow paths so that the solution receives centrifugal force by the rotation of the substrate (described later for detail). The volume of solution subjected to the centrifugal force increases when the imaginary chamber length is longer. That is, solution in chambers easily flows in flow paths when the imaginary chamber lengths are longer. With the substrate of the present invention, the "first imaginary chamber length" is longer than the "second imaginary chamber length," so that it is possible to make greater the force (centrifugal force) required to allow the solution in the second chamber to flow in the second flow path than the force (centrifugal force) required to allow the solution in the first chamber to flow in the first flow path. Therefore, by controlling centrifugal force (i.e. the rotation speed of the substrate), it is possible to transfer liquid stepwise from the first chamber to the second chamber, and from the second chamber to the third chamber.

Examples of the method of making longer the "first imaginary chamber length" than the "second imaginary chamber length," include (1) making narrower the width of the first chamber than the width of second chamber and (2) making shallower the depth of the first chamber than the depth of the second chamber. These two methods are by no means limited, and, for example, (1) and (2) may be combined.

(1) Making Narrower the Width of the First Chamber than the Width of the Second Chamber It is not necessary to make narrower the width of the entire first chamber than the width of the second chamber. The first imaginary chamber length may only be made longer than the second imaginary chamber length, so that at least the width of the first chamber near the first flow path end part is preferably narrower than the width of second chamber near the third flow path end part. Further, it is preferable to make the width of the first chamber near the first flow path end part wider than the width of the first flow path near the first flow path end part.

(2) Making Shallower the Depth of the First Chamber than the Depth of the Second Chamber It is not necessary to make shallower the depth of the entire first chamber than the depth of the second chamber. The first imaginary chamber length may only be made longer than the second imaginary chamber length, so that at least the depth of the first chamber near the first flow path end part is preferably shallower than the depth of the second chamber near the third flow path end part. Further, it is preferable to make that the depth of the first chamber near the first flow path end part deeper than the depth of the first flow path near the first flow path end part.

A chamber has a greater volume than a flow path, so that the width and depth of chambers is adjusted easier than the width and depth of a flow path.

Each flow path in the substrate of the present invention is required to be very thin, to produce adequate capillary force and retain solution in a chamber. To be more specific, the width of the first flow path and the second flow path is preferably, for example, between 4 μm and 2000 μm. The first flow path may have the same cross-sectional area as the second flow path, and may have the same width and depth. The width and depth of the flow paths are the same, so that the production of the flow paths is easy and the production process does not involve a load.

The shape of each flow path in the present invention is not particularly limited, and adjusted adequately. For example, when a biological sample such as blood plasma flows in a micro-flow path (e.g. a micro flow-path having a width between 4 μm and 60 μm inclusive), the biological sample flows little due to its viscosity, and, furthermore, proteins contained in the biological sample adhere to the interior walls of the micro-flow path, and therefore the biological sample may clog the micro flow-path. For that reason, by adjusting the shape of miniature micro-flow paths adequately, it is preferable to reliably transfer a biological sample such as blood plasma stepwise smoothly.

For reliably transferring liquid such as a biological sample, it is preferable to make the cross-sectional area of the first flow path near the first flow path end part and the cross-sectional area of the second flow path near the third flow path end part, constant or larger in the centrifugal direction; or make the cross-sectional area of the first flow path near the second flow path end part and the cross-sectional area of the second flow path near the fourth flow path end part larger in the centrifugal direction. The cross-sectional area of the first flow path may increase gradually from the first flow path end part to the second flow path end part, or cross-sectional area of the second flow path may increase gradually from the third flow path end part to the fourth flow path end part.

In this way, by adjusting the shapes of end parts of each flow path (the size of cross-sectional area of each micro-flow path), it is possible to reliably transfer biological samples in a flow path part in the substrate of the present invention, even when the width of the first flow path except for the first flow path end part and the second flow path end part, and the width of the second flow path except for the third flow path end part and the fourth flow path end part, are 4 µm or more and less than 60 µm. Similarly, by adjusting the shapes (the size of cross-sectional area) of end parts of each flow path, it is possible to reliably transfer biological samples in flow path parts in the substrate of the present invention, even when the depth of the first flow path except for the first flow path end part and the second flow path end part, and the depth of the second flow path except for the third flow path end part and the fourth flow path end part, are 4 µm or more and less than 60 µm.

The interior walls of the first flow path end part and the third flow path end part, and (if there is) a fifth flow path end part (described later) (i.e. the upstream end parts of the flow paths) are preferably hydrophobic, in order to prevent a solution in chambers from flowing into the flow paths without receiving centrifugal force by allowing the flow path parts to be wet.

To make the flow path end parts hydrophobic, the flow path end parts may be made from hydrophobic materials or hydrophobic treatment may be applied to the inner walls of the flow path parts. When the upstream end parts of flow paths are hydrophobic, a solution accommodated in chambers can be retained in the end parts. To be more specific, when the cross-sectional area of each flow path is small enough and the flow path end part is hydrophobic, the solution does not intrude in the flow path by a surface tension, and is retained in the flow path end part.

Further, the entire face of interior walls of each flow path may be hydrophobic. By making the entire surface of interior walls of each flow path hydrophobic, a solution in a chamber is retained entirely in the flow path, not only retained in flow path end parts, so that holding power increases. In cases where each flow path is entirely hydrophobic, it is possible to transfer the desired amount of solution in a chamber to the next chambers by a rotation of the substrate in a predetermined duration. Therefore, by controlling the duration of rotation, it is possible to transfer a desired amount of solution through chambers more accurately. In addition, by controlling the time it takes to transfer a desired amount of solution through chambers, it is possible to control the time to carry out a reaction in each chamber.

Further, the interior walls of a flow path part (including chambers) may be entirely hydrophobic. Furthermore, by forming the substrate from hydrophobic materials, it is possible to make all interior walls in a flow path part hydrophobic. Consequently, productivity of the substrate improves.

Examples of hydrophobic materials include: semiconductor materials represented by, for example, a single crystal silicon, amorphous silicon, silicon carbide, silicon oxide and silicon nitride; inorganic insulation materials selected from a group of alumina, sapphire, forsterite, silicon carbide, silicon oxide and silicon nitride; and organic materials selected from a group of polyethylene, polypropylene, polyisobutylene, polyethylene terephthalate (PET), unsaturated polyester, fluorine-containing resin, polyvinyl chloride, polyvinylidene chloride, polyvinyl acetate, polyvinyl alcohol, polyvinyl acetal, acrylic resin, polyacrylonitrile, polystyrene, acetal resin, polycarbonate (PC), polyamide, phenolic resin, urea resin, epoxy resin, melamine resin, styrene-acrylonitrile copolymer, acrylonitrile butadiene styrene copolymer, silicone resin, polyphenylene oxide and polysulphone. The materials that are suitable for use include PET and PC.

Examples of providing a hydrophobic treatment include applying a fluorine-containing resin, silicone-containing resin and so on. Preferably, a fluorine-containing resin is applied.

Flow path parts of the substrate of the present invention may have a plurality of second chambers, for example, a second chamber A and a second chamber B.

The third flow path has a fifth flow path end part connected with the second chamber A and a sixth flow path end part connected with the second chamber B. The features of the fifth flow path end part is that the fifth flow path end part is placed in a position distant from the center of rotation in the second chamber A and not placed on the straight line that connects the axis of rotation and the second flow path end part.

When there are the second chamber A and the second chamber B in flow path parts of the substrate, "a second A imaginary chamber length" is made longer than "a second B imaginary chamber length". "The second A imaginary chamber length" refers to the distance from the fifth flow path end part to the surface of solution along the direction toward the center of rotation of the substrate (i.e. the centripetal direction) when the certain amount of solution (also referred to as "imaginary chamber volume") is accommodated in the second chamber A and the substrate is rotated about the axis of rotation to form the surface of solution. "The second B imaginary chamber length" refers to the distance from the sixth flow path end part to the surface of solution along the direction toward the center of rotation of the substrate (i.e. the centripetal direction) when the certain amount of solution (also referred to as "imaginary chamber volume") is accommodated in the second chamber B and the substrate is rotated about the axis of rotation to form the surface of solution.

By increasing the number of the second chambers, it is possible to increase the number of stages in liquid transfer. Therefore, it is possible to increase functions of stirring solutions to transfer, allowing the solutions to react with chemical substances and so on, thereby carrying out complicated processes easily in one flow path part.

The substrate of the present invention may have two or more flow path parts. As described above, each flow path part has the first to third chambers, and the first and second flow paths. Further, each flow path part has a third flow path when they have a plurality of second chambers.

With using a substrate having two or more flow path parts, it is possible to allow centrifugal force to work on two or more flow path parts at the same time by the rotation of the substrate. For example, by applying the first rotation speed, it is possible to transfer liquid in the first chambers to the second chambers at the same time. Therefore, it is possible to increase the number of processes in parallel, thereby processing a great number of samples in a short time. Consequently, by integrating flow path parts, it is possible to increase the number of processes in parallel, thereby processing a great number of samples in a short time.

Further, every flow path part has different chambers and structures, so that it is possible to individually control liquid transfer on a per flow path part basis. Consequently, it is possible to perform a plurality of types of measurement sequences with one substrate. For example, measuring glucose of a one-step reaction in flow path part 1 and measuring cholesterol of a three-step reaction in flow path part 2.

Forming a plurality of flow path parts in one substrate is effective in lowering the cost to process sample from the perspective of the manufacturing cost of the substrate.

The substrate of the present invention may have a central shaft that works as the axis of rotation. By having a central shaft, the substrate itself can rotate directly without preparing a mechanism to mount on the rotation drive part, so that the liquid transfer apparatus becomes more convenient. Further, from the perspective of the manufacturing cost, this configuration lowers the cost to process sample.

2. The Liquid Transfer Method of the Present Invention

The liquid transfer method of the present invention includes transferring a solution to chambers included in flow path parts in the substrate of the present invention. Now, the liquid transfer method of the present invention will be described below including its basic mechanisms.

The liquid transfer method of the present invention includes the steps of: (A) rotating the substrate of the present invention around the axis of rotation at the first rotation speed rpm and (B) rotating the substrate at the higher second rotation speed $rpm_2$ than the first rotation speed $rpm_1$, and transfers liquid stepwise to chambers in flow path parts in the substrate.

The solution that is injected in the first chamber in a flow path part in the substrate of the present invention via a injection inlet is retained in the first flow path end part on the first flow path by capillary force. The capillary force then is called "the first capillary force." When the substrate rotates in the direction of rotation at the first rotation speed, the first centrifugal force works on the solution retained in the first flow path end part along the centrifugal direction (i.e. the direction to part from the axis of rotation). The volume of the solution which the first centrifugal force works on corresponds to the three-dimensional volume in which the cross-section of the first flow path end part is the bottom and in which the first imaginary chamber length (described before) is the height. When the first centrifugal force exceeds the first capillary force, the solution in the first chamber flows in the first flow path, to be transferred to the second chamber. Air in the second chamber is exhausted outside via an air opening.

The third flow path end part, which is the inlet end part of the second flow path, is not placed on the straight line that connects the center of rotation and the second flow path end part, which is the outlet end part of the first flow path. Therefore, the solution that flows in the second chamber from the first flow path receives the "second capillary force" in the third flow path end part.

By equalizing the cross-sectional area of the first flow path and the cross-sectional area of the second flow path, it is possible to make equal the second capillary force and the first capillary force. Meanwhile, the second centrifugal force that is produced on the third flow path end part usually becomes greater than the first centrifugal force, because the third flow path end part is more distant from the rotating shaft.

As described before, the "second imaginary chamber length" of the second chamber is shorter than the "first imaginary chamber length" of the first chamber. The volume of solution subjected to the second centrifugal force corresponds to three-dimensional volume in which the cross-section of the third flow path end part is the bottom and in which the second imaginary chamber length is the height, and therefore is smaller than the volume of solution that receives the first centrifugal force in the first chamber.

When the difference between the volume of solution that receives the first centrifugal force in the first chamber and the volume of solution that receives the second centrifugal force in the second chamber is great, this difference can cancel out the difference between the first centrifugal force and the second centrifugal force due to the difference in the distance from the rotating shaft. Therefore, the solution having flown in the second chamber does not flow in the second flow path depending on the first rotation speed, and is retained in the second chamber on a temporary basis.

Then, the second centrifugal force produced by rotation at the second rotation speed $rpm_2$, which is higher than the first rotation speed $rpm_1$, exceeds the second capillary force. As a result, the solution in the second chamber flows in the second flow path, to be transferred to the third chamber. Air in the third chamber is exhausted outside via an air opening.

In this way, when the substrate rotates at the first rotation speed $rpm_1$, the solution that flows in the first chamber is transferred from the first chamber to the second chamber, to be retained in the second chamber. Next, when the rotation speed is changed to the second rotation speed $rpm_2$, which is higher rotation speed than the first rotation speed $rpm_1$, the solution is transferred from the second chamber to the third chamber. In this way, by controlling the rotation speed, it is possible to transfer the solution stepwise to each chamber in the flow path parts of the substrate. The rotation speed $rpm_1$ and $rpm_2$ are preferably set in the range of 600 to 10000 rpm, and, more preferably, set in the range of 1000 to 5000 rpm.

The difference between rotation speed $rpm_1$ and rotation speed $rpm_2$ is preferably set at 200 rpm or more, and, more preferably, at 400 rpm or more. There are variations of physical properties of a human blood plasma sample being a biological sample, between individuals or between days of an individual. By setting the difference in rotation speed 400 rpm or more, it is possible to perform control of transferring biological sample unaffected by the variation, and it is easy to control rotation by the apparatus. Certainly, by providing the means for detecting start of liquid transfer and the means for feeding back the detection to a rotation control mechanism for the apparatus, the variations can be resolved. In that case, from the perspective of the response of feedback control, the difference in the rotation speed is also preferably set at 200 rpm or more, so that transfer of a solution is realized more accurately.

As shown in Embodiment 3 (described later), in cases where the difference of rotation speed is reduced (e.g. from 400 to 200 rpm), it is possible to control the starts of liquid transfer even when a plurality of second chambers are placed, so that multistage liquid transfer can be realized more at ease. Thereby the solution to be transferred can be subjected to multiple-step treatments.

3. The Liquid Transfer Apparatus of the Present Invention

The apparatus of the present invention has: the substrate described before; and a rotation drive part that rotates the substrate around the center of rotation. By using the liquid transfer apparatus, it is possible to transfer liquid stepwise to the chambers in flow path parts in the substrate.

The rotation drive part of the liquid transfer apparatus may include a motor that rotates the substrate around the axis of rotation and a speed characteristic application section that gives speed characteristics to the motor, thereby applying predetermined rotation drive speed to the substrate and allowing multistage liquid transfer more reliably.

Examples of a motor that rotates the substrate include, for example, a DC motor, DC brushless motor, AC motor and step motor. A step motor is preferable because sudden rotation and braking of the substrate are easily realized only by applying driving signals from outside. Further, a DC motor does not particularly require a driving circuit (see FIG. 1). In the case where a DC brushless motor is employed, faster sudden braking is realized when the driving circuit (see FIG. 1) has a function of applying reverse rotation voltage.

The rotation drive part of the liquid transfer apparatus preferably has a rotation speed detector that detects the rotation speed of the substrate during rotation, and a rotation speed control section that corrects the speed characteristics given to the motor by the speed characteristic application section based on the rotation speed detected by the rotation speed detector. The rotation drive part drives the substrate in rotation while the actual rotation speed is fed back to correct speed characteristics, so that the amount of liquid transfer is stabilized and the repeatability of the liquid transfer improves.

Next, embodiments of the present invention will be described in detail with reference to the accompanying drawings.

Embodiment 1

Figure 2:
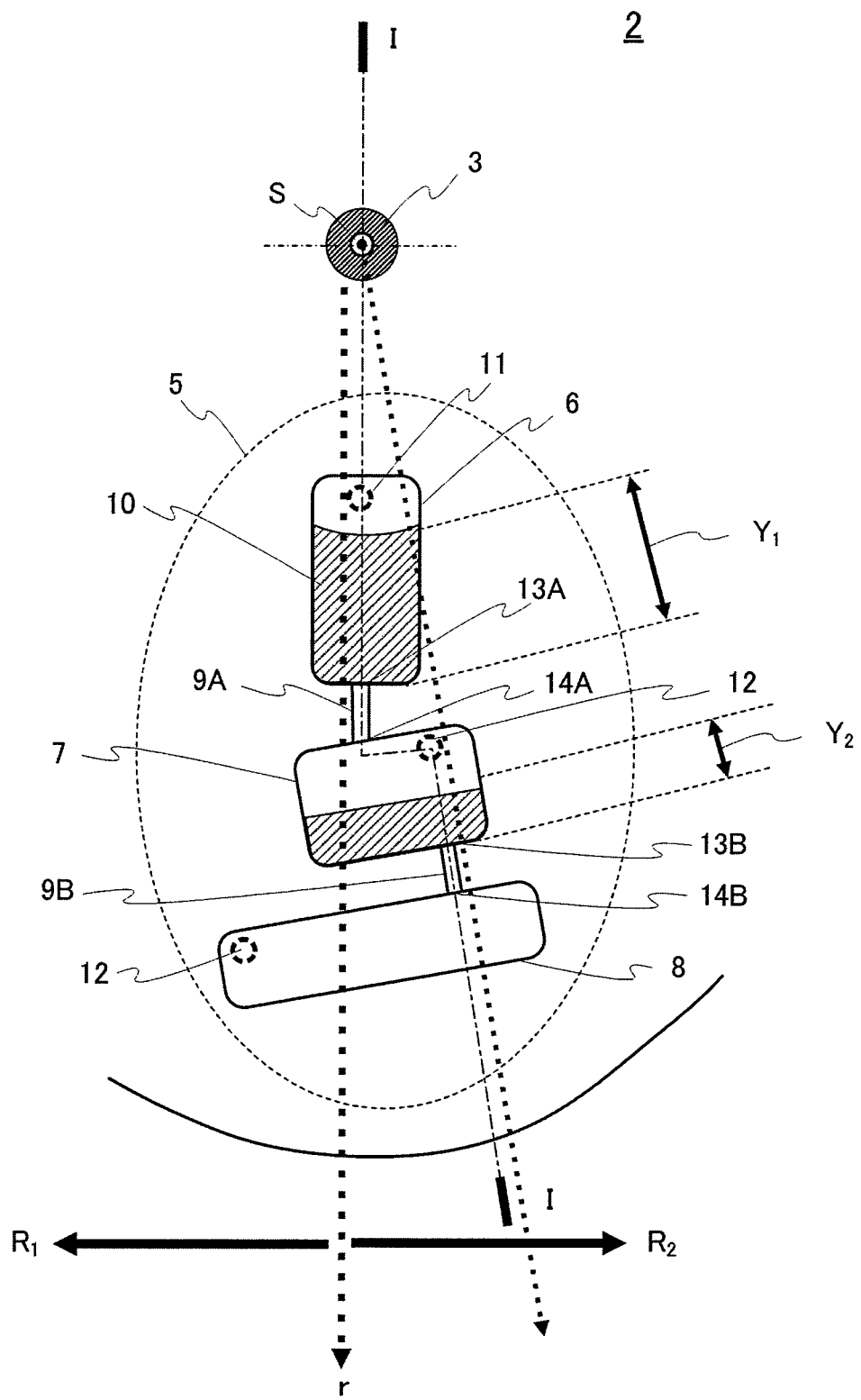
FIG. 2 is a partial expanded plan view of the substrate according to Embodiment 1.

FIGS. 1 to 4 show liquid transfer apparatus 1 of the present invention. Liquid transfer apparatus 1 includes substrate 2 and rotation drive part 4. FIG. 2 shows solution 10 to explain first imaginary chamber length $Y_1$ and second imaginary chamber length $Y_2$.

Liquid transfer apparatus 1 shown in FIG. 1 has substrate 2; and rotation drive part 4 that rotates rotating shaft 3 fixing substrate 2. The axis of rotation (axis) S of rotating shaft 3 extends vertically. Substrate 2 is fixed at the upper end part of rotating shaft 3. Substrate 2 is a circle in a plan view, and the center of substrate 2 is placed on the axis of rotation S of rotating shaft 3. Meanwhile, the bottom end part of rotating shaft 3 is connected with motor 31. An outer shape of substrate 2 is set arbitrary so as to accommodate flow path parts 5, and, for example, if the outer shape is a circle, the diameter is set approximately between 10 mm and 150 mm. Further, it is preferable to set the thickness of substrate 2 approximately between 0.1 mm and 30 mm.

Substrate 2 rotates together with rotating shaft 3. As arrows R1 and R2 shown in FIG. 2, the rotating directions of rotating shaft 3 are defined as directions to intersect with radial directions r of rotating shaft 3. That is, the rotating directions are defined as being perpendicular to an imaginary line intersecting with the axis of rotation S of rotating shaft 3 at right angles and as sharing the same plane with the imaginary line. Substrate 2 is rotatable clockwise direction R1 or counterclockwise direction R2 in a plan view.

Rotation drive part 4 shown in FIG. 1 is connected with rotating shaft 3 mechanically. Rotation drive part 4 has: rotating shaft 3; motor 31 that rotates a substrate fixed to rotating shaft 3; and driving circuit 32 of motor 31. Further, rotation drive part 4 has: control signal output section 33 that outputs control signals; speed characteristic application section 34 that gives driving circuit 32 of motor 31 to desired motor speed characteristic (e.g. see FIG. 9) based on the control signals received as input from control signal output section 33. Control signal output section 33 may be another computer apart from liquid transfer apparatus 1.

Rotation drive part 4 may have rotation speed detector 35 that detects the rotation speed of substrate 2 during rotation and rotation speed control section 36 that corrects speed characteristic application section 34. The actual rotation speed of substrate 2 detected by rotation speed control section 36 is sent to rotation speed control section 36. When there is a difference between the received actual rotation speed and the speed characteristic that should be given to motor 31 by speed characteristic application section 34, the speed characteristic given by speed characteristic application section 34 is corrected by rotation speed control section 36. In this way, by driving substrate 2 while the actual rotation speed is fed back to correct speed characteristics, the stable liquid transfer is realized and the repeatability of liquid transfer improves.

A plurality of flow path parts 5 are included in the substrate shown in FIG. 1. Flow path parts 5 are arranged radially around rotating shaft 3.

In FIG. 2, one of flow path parts 5 is shown schematically. Flow path part 5 has: supply source chamber 6 of the first chamber and supply destination chamber 7 of a second chamber; final stage chamber 8 of a third chamber; first flow path 9A and second flow path 9B.

[Supply Source Chamber 6]

Solution 10 is injected in supply source chamber 6, which is the target to be transferred to chambers. Supply source chamber 6, which is formed inside substrate 2, is spatially closed. However, injection inlet 11 having a circular cross-section is formed on supply source chamber 6, and communicates the interior of chamber 6 and the exterior substrate 2. This injection inlet 11 is used for injecting solution 10 into supply source chamber 6.

Supply source chamber 6 shown in FIG. 2 has a shape of a substantially rectangular shape in a plan view. First flow path end part 13A (an opening part) connected with first flow path 9A is placed in a side wall that is placed in a far part from rotating shaft 3. Injection inlet 11 is placed in a position nearer rotating shaft 3 than first flow path end part 13A, and, to be more specific, placed in a top corner of supply source chamber 6 shown in FIG. 2. The area of injection inlet 11 in a plan view is substantially smaller than the area of supply source chamber 6 in a plan view.

By setting the position and area of injection inlet 11 in this way, it is possible to reduce leakage or scatter of solution 10 through injection inlet 11 by centrifugal force that works by the rotation of substrate 2 (outward force in radial direction r). For that reason, it is possible to inject solution 10 into supply source chamber 6 and rotate substrate 2 while injection inlet 11 is open. In contraries, in cases where injection inlet 11 is placed in a position more distant from rotating shaft 3 than first flow path end part 13A or where the area of injection inlet 11 is relatively large with respect to the area of supply source chamber 6, injection inlet 11 is preferably sealed when substrate 2 is rotated, in order to prevent solution 10 in supply source chamber 6 from leaking or scattering through injection inlet 11.

The dimensions and volume of supply source chamber 6 need to be determined according to the liquid volume of sample (i.e. solution 10), and the volume of supply source chamber 6 is preferably between 0.1 µl and 100 µL.

[Supply Destination Chamber 7]

In supply destination chamber 7, solution 10 flows from supply source chamber 6 via first flow path 9A. Supply destination chamber 7 is aligned with supply source chamber 6 in radial direction r and placed more distant from rotating shaft 3 than supply source chamber 6. Supply destination chamber 7 is formed inside substrate 2, and may be spatially closed, or have air opening 12.

Outlet end part (second flow path end part) 14A of first flow path 9A is placed in the side wall on the nearer side from rotating shaft 3 of supply destination chamber 7 in a plan view. Furthermore, inlet end part (third flow path end part) 13B of second flow path 9B is placed in a side wall on the farther side from rotating shaft 3 of supply destination chamber 7 in a plan view.

Supply destination chamber 7 shown in FIG. 2 has a shape of a substantially rectangular shape in a plan view. Chamber width 22 of supply destination chamber 7 is wider than chamber width 21 of supply source chamber 6 (see FIG. 3B).

The dimensions and volume of supply destination chamber 7 need to be determined according to the liquid volume of a sample (i.e. solution 10), and the volume of supply destination chamber 7 is preferably between 0.1 μL and 100 μL.

[Final Stage Chamber 8]

In final stage chamber 8, solution 10 is transferred from supply destination chamber 7 via second flow path 9B. Final stage chamber 8 is aligned with supply destination chamber 6 in radial direction r and placed more distant from rotating shaft 3 than supply destination chamber 7.

Final stage chamber 8 is formed inside substrate 2, and spatially closed. Air opening 12 having a circular cross-section is formed, which communicates the interior of final stage chamber 8 and the exterior substrate 2. Air opening 12 has functions of letting the air in supply destination chamber 7 and final stage chamber 8 out to the outside of substrate 2 when solution 10 flows in supply destination chamber 7 and final stage chamber 8.

Air opening 12 is provided in the upper left corner of final stage chamber 8 shown in FIG. 2. To reduce leakage or scatter of solution 10 through air opening 12 by centrifugal force that works during the rotation of substrate 2, the area of air opening 12 in a plan view is substantially made smaller than the area of final stage chamber 8 in a plan view.

Final stage chamber 8 has a shape of a substantially rectangular shape in a plan view. Chamber width 23 of final stage chamber 8 is wider than chamber width 22 of supply destination chamber 7 (see FIG. 3B). The width and depth of final stage chamber 8 are not particularly limited, and may be set arbitrarily as long as final stage chamber 8 has a volume to accommodate solution 10 that flows in final stage chamber 8. Outlet end part (fourth flow path end part) 14B of flow path 9B is placed on the side wall of final stage chamber 8 on the rotating shaft 3 side in a plan view.

The dimensions and volume of final stage chamber 8 need to be determined according to the liquid volume of a sample (i.e. solution 10), and the volume of final stage chamber 8 is preferably between 0.1 μL and 100 μL.

Further, a plurality of third chambers 8 may be communicated with a plurality of flow paths 9B and placed.

[First Flow Path 9A]

First flow path 9A is a flow path for connecting source chamber 6 and supply destination chamber 7 each other in fluid communication. First flow path 9A, which is formed inside substrate 2, is spatially closed. Further, both ends of flow path 9A, that is, first flow path end part 13A and second flow path end part 14A are connected with supply source chamber 6 and supply destination chamber 7, respectively.

First flow path 9A need to be very thin so that solution 10 is sure to be transferred from supply source chamber 6 to supply destination chamber 7 via first flow path 9A. To be more specific, the volume of first flow path 9A is preferably the same or less than the volumes of supply source chamber 6 and supply destination chamber 7.

Further, the width of first flow path 9A is preferably narrower than the widths of supply source chamber 6 and supply destination chamber 7. For example, the preferable width of flow path 9A is approximately between 4 μm and 2000 μm, more preferably, approximately between 100 μm and 300 μm. The depth of flow path 9A is preferably shallower than the depths of supply source chamber 6 and supply destination chamber 7. For example, when the width of flow path 9A is approximately between 10 μm and 500 μm, the preferable depth of flow path 9A is approximately between 10 μm and 100 μm. The width and depth of a flow path may be adjusted from limits for producing the flow path and from the perspectives of adequately generating capillary force.

First flow path end part 13A of first flow path 9A connected with supply source chamber 6 can function as a valve of solution 10 accommodated in supply source chamber 6. First flow path 9A extends along the centrifugal direction from first flow path end part 13A, so that the centrifugal force that works on solution 10 when substrate 2 rotates allows solution 10 in supply source chamber 6 to flow in first flow path 9A. To allow all the solution that is farther from the center of rotation beyond injection inlet 11 in supply source chamber 6 to flow in flow path 9A by centrifugal force, it is preferable to place first flow path end part 13A around the outermost periphery of chamber 6, which is the farthest from the center of rotation.

First flow path 9A extends along the centrifugal direction from the near side to rotating shaft 3 and is connected with second flow path end part 14A. This prevents the solution having flown in supply destination chamber 7 on a temporary basis from running back through flow path 9A toward supply source chamber 6. In this way, first flow path 9A may only extend along the centrifugal direction, so that first flow path 9A has higher degrees of design freedom, which is preferable from the perspective of productivity.

[Second Flow Path 9B]

Second flow path 9B is a flow path for connecting destination chamber 7 and final stage chamber 8 each other in fluid communication. Second flow path 9B, which is formed inside substrate 2, is spatially closed. Further, both ends of flow path 9B, that is, third flow path end part 13B and fourth flow path end part 14B, are connected with supply destination chamber 7 and final stage chamber 8, respectively.

Third flow path end part 13B is not on the straight line that connects rotating shaft 3 and second flow path end part 14A. By shifting third flow path end part 13B from the straight line, solution 10 having flown in supply destination chamber 7 via flow path 9A cannot directly flow in second flow path 9B, and stays in supply destination chamber 7 on a temporary basis.

First flow path 9B need to be very thin so that solution 10 is sure to be transferred from supply destination chamber 7 to final stage chamber 8 via flow path 9B. The cross-sectional area of third flow path end part may be made the same, greater, or less than that of the first flow path end. Preferable volume, width and depth of flow path 9B are preferably the same as those of flow path 9A approximately.

Third flow path end part 13B of second flow path 9B connected with supply destination chamber 7 can function as a valve of solution 10 accommodated in supply destination chamber 7. Second flow path 9B extends along the centrifugal direction from third flow path end part 13B, so that, by raising the rate of rotation of substrate 2 to make centrifugal force working on solution 10 large, it is possible to allow solution 10 in supply destination chamber 7 to flow in second flow path 9B.

Second flow path 9B extends along the centrifugal direction and is connected with fourth flow path end part 14B. This prevents the solution having flown in final stage chamber 8 on a temporary basis from running back through flow path 9B toward supply destination chamber 7.

[Walls Configuring Flow Path Part 5]

It is preferable that the walls of first flow path end part 13A of first flow path 9A and the walls of third flow path end part 13B of second flow path 9B are made from hydrophobic materials or subjected to hydrophobic treatment. By making first flow path end part 13A and third flow path end part 13B hydrophobic, the solutions accommodated in supply source chamber 6 and supply destination chamber 7, respectively, are retained easily by capillary force.

It is preferable that the static contact angles of water on the walls of first flow path end part 13A of first flow path 9A and the walls of third flow path end part 13B of second flow path 9B are between 35° and 120°. In cases where the walls of the flow paths have a contact angle of about 35° or less, a solution can intrude in the flow paths from first flow path end part 13A and third flow path end part 13B by capillary action even when the substrate does not rotate. In cases where the walls of the flow paths have a contact angle of about 120° or more, the walls are too water-repellent, and therefore, a solution can not intrude in the flow paths from first flow path end part 13A or third flow path end part 13B even when the maximum rotation speed is applied. The static contact angles of water on the walls of first flow path end part 13A of first flow path 9A and the walls of third flow path end part 13B of second flow path 9B are preferably between 66° and 90°. One example is that, when the static contact angle of water on the walls of flow paths is set in 66° from 82°, the rotation speed upon starting transfer of the solution decreases by 45%. Therefore, to increase the number of stages of chambers, it is more desirable that the walls of flow paths are hydrophobic such that the contact angle of water is 90°.

Meanwhile, inner walls of flow path part 5 except for the walls of first flow path end part 13A and the walls of third flow path end part 13B (also referred to as the "remaining part") may be hydrophobic or hydrophilic. "Remaining part" includes the walls of supply source chamber 6, supply destination chamber 7 and final stage chamber 8, all walls of first flow path 9A (i.e. including second flow path end part 14A) except for first flow path end part 13A and all walls of second flow path 9B (i.e. including fourth flow path end part 14B) except for second flow path end part 13B. In cases where the remaining part is hydrophilic, a solution having flown in first flow path 9A from supply source chamber 6, or a solution having flown in second flow path 9B from supply destination chamber 7 is sure to flow into supply destination chamber 7 or final stage chamber 8 by humidifying effect and capillary action.

Here, it is preferable that the contact angles of water on the walls of supply source chamber 6, supply destination chamber 7 and final stage chamber 8 are approximately between 45° and 105°. When the contact angles of the chamber walls are 45° or less, by hydrophilicity of the side walls of chambers, the surface of a solution retained in chambers becomes a concave shape in a plan view. When the solution surface is concave, the imaginary chamber lengths become short. The curvature of the concave surface increases when the width of a chamber is narrower, and particularly, remarkably increases at a low rotation speed. For this reason, the difference between the first imaginary chamber length and the second imaginary chamber length decreases, and therefore it is difficult to realize stepwise liquid transfer.

One example is that, when the contact angle of 5 μL of solution injected in supply source chamber 6 having a width of 2 mm is 65°, the first imaginary chamber length decreases by 0.4 mm and the difference between the first rotation speed and the second rotation speed decreases by 80 rpm due to the curvature of the solution surface. Meanwhile, when the contact angle of 5 μL of a solution injected in supply source chamber 6 having a width of 2 mm is 45°, the solution flowing out from supply source chamber 6 at the first rotation speed is transferred to the final stage chamber without retaining in supply destination chamber 7, and therefore stepwise liquid transfer is not realized. Further, when the contact angle of 5 μL of a solution injected in supply source chamber 6 having a width of 2 mm is 105° or more, the first imaginary chamber length decreases by 0.3 mm and the first rotation speed decreases by 200 rpm due to the curvature of the solution surface having a convex shape, and therefore stepwise liquid transfer is not realized.

To provide hydrophilicity, the part may be made from hydrophilic materials or hydrophilic treatment may be applied to the part. Examples of hydrophilic materials include glass, quartz glass and metal materials such as aluminum, copper, and stainless steel. Surfaces of the metal materials have to be clean by excluding organic substances that adhere to the surface in advance. Examples of hydrophilization treatment include applying a surfactant represented by TritonX-100 and applying high polymer having hydrophilic groups such as a hydroxyl group, a sulfonic group and a carboxyl group. Preferably, a surfactant is applied. It should be noted that the above hydrophilic treatment can make the walls of first flow path end part 13A of first flow path 9A and the walls of third flow path end part 13B of second flow path 9B hydrophilic. In particular, it is noted that, hydrophilic agents dissolving from the walls of supply source chamber 6 applied near first flow path end part 13A of first flow path 9A can make the walls of first flow path end part 13A hydrophilic. Therefore, it is preferable that the hydrophilic agent being hard to elute from the applied surface is used.

The First Example of Layered Structure of Substrate 2

Figure 3A:
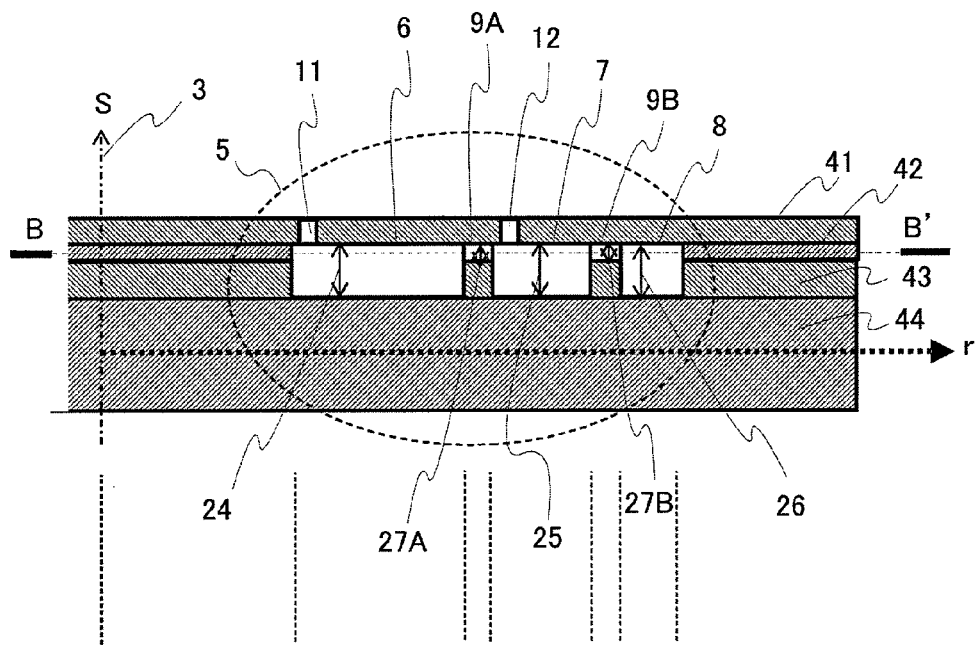
FIG. 3 is a partial cross-sectional view (FIG. 3A) along I-I line in FIG. 2, and a corresponding plan view (FIG. 3B)
Figure 3B:
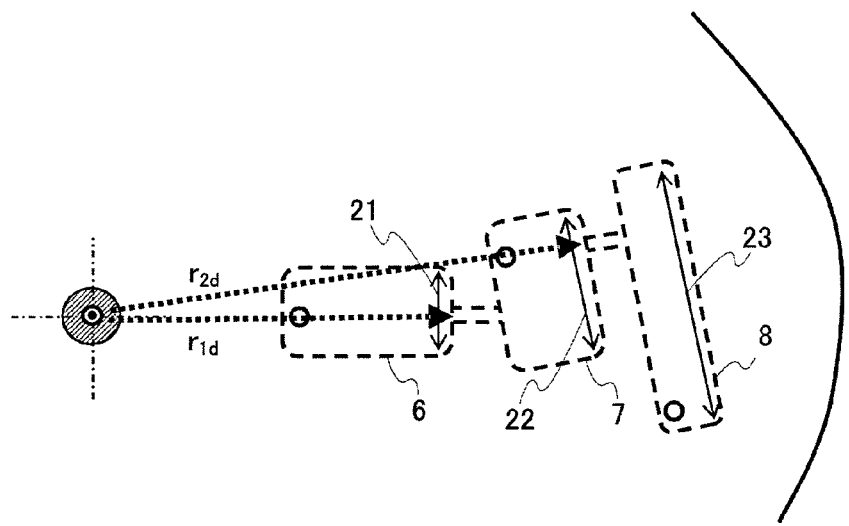
Figure 4:
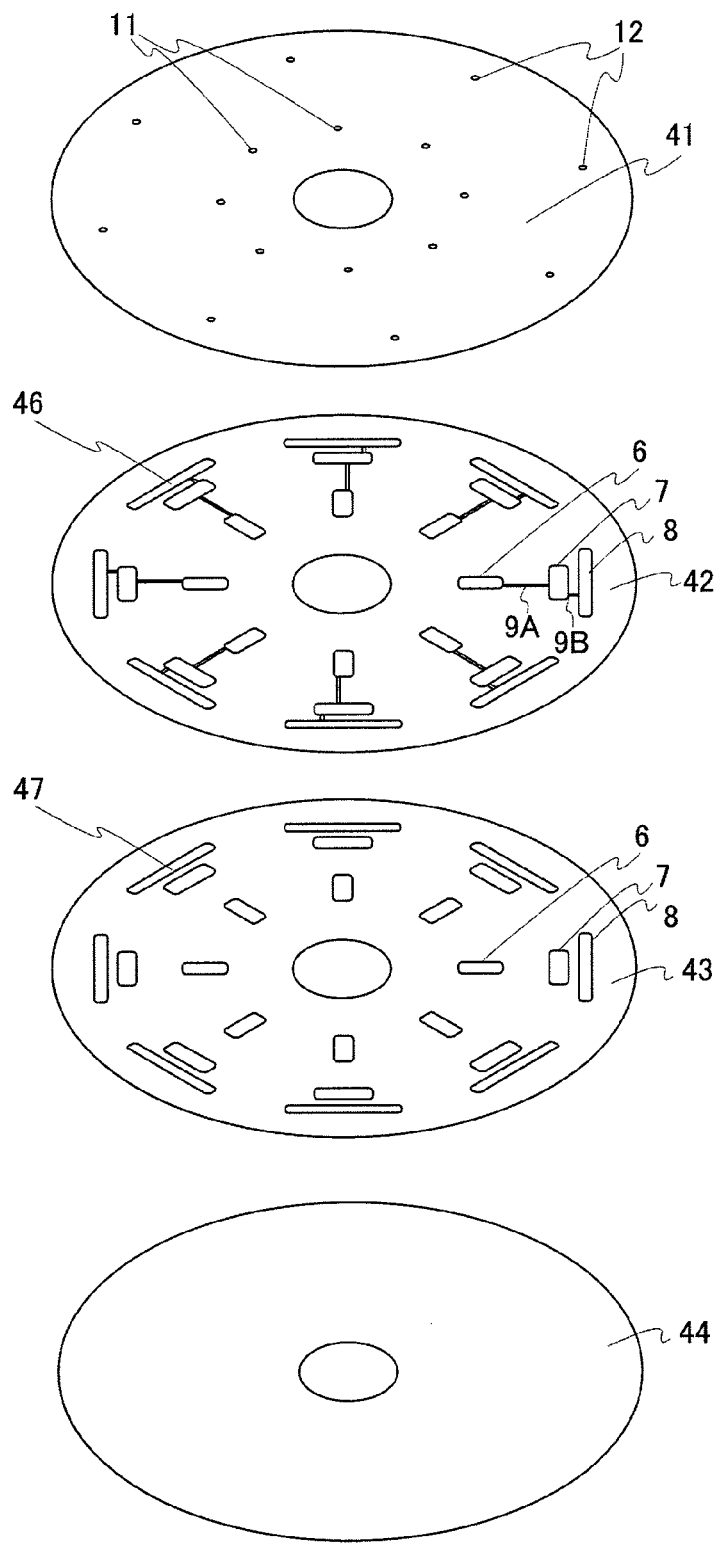
FIG. 4 is an exploded perspective view of the first example of the substrate.

Substrate 2 may have layered structure as shown in FIGS. 3A and 4. Substrate 2 has a four-layer structure, and includes upper plate material 41, flow path plate material 42, chamber plate material 43 and lower plate material 44.

Upper plate material 41 has injection inlet 11 and air opening 12 that penetrate the upper plate material in the thickness direction. Flow path plate material 42 has groove hole 46 that penetrates the flow path plate material in the thickness direction. Groove hole 46 has a shape corresponding to supply source chamber 6, supply destination chamber 7, final stage chamber 8, flow path 9A and flow path 9B. Chamber plate material 43 has groove hole 47 that penetrates the chamber plate material in the thickness direction. Groove hole 47 has a shape corresponding to supply source chamber 6, supply destination chamber 7 and final stage chamber 8. Lower plate material 44 constitutes the bottom surface of supply source chamber 6, supply destination chamber 7 and final stage chamber 8, and grooves or holes are not provided in lower plate material 44.

Substrate 2 having a four-layered structure can be formed by stacking the plate materials, so that the substrate is excellent in terms of productivity. The depth of flow paths 9A and 9B is determined by the thickness of flow path plate material 42. Further, the depth of supply source chamber 6, supply destination chamber 7 and final stage chamber 8 is determined by the total of the thickness of flow path plate material 42 and the thickness of chamber plate material 43. Therefore, the depth of flow path 9A and flow path 9B is made easier than the depth of supply source chamber 6, supply destination chamber 7 and final stage chamber 8. Also, the depth of flow path 9A and flow path 9B, and the depth of supply source chamber 6, supply destination chamber 7 and final stage chamber 8 can be set individually.

For example, the depth of flow path 9A and flow path 9B is about 100 μm, so that it is possible to form a substrate easily by using flow path plate material 42 in which groove hole 46 having a shape of flow paths 9A and 9b, and, supply source chamber 6, supply destination chamber 7 and final stage chamber 8 is formed. This is preferable from the perspective of productivity.

Further, lower plate material 44, which is made to be the bottom surface of supply source chamber 6 and supply destination chamber 7, is a separate member from other plate materials, so that the lower plate material 44 is allowed to carry reaction reagents easily before stacking. For example, reaction reagents can be carried in the bottom part of supply destination chamber 7 for the purpose of carrying out a reaction with a solution transferred from supply source chamber 6.

To stack the plate materials, arbitrary methods may be employed. For example, adhesive material or adhesive sheet may be interposed between the plate materials, and other methods such as ultrasonic bonding, thermocompression bonding and lamination may be employed. To form flow paths and chambers, arbitrary methods may be employed. Photolithography represented by semiconductor micromachining technology, injection molding represented by plastic molding, cutting, and transcription for making duplicates from a master, are examples. Photolithography is preferable for use.

A Second Example of Layered Structure of Substrate 2

Figure 5:
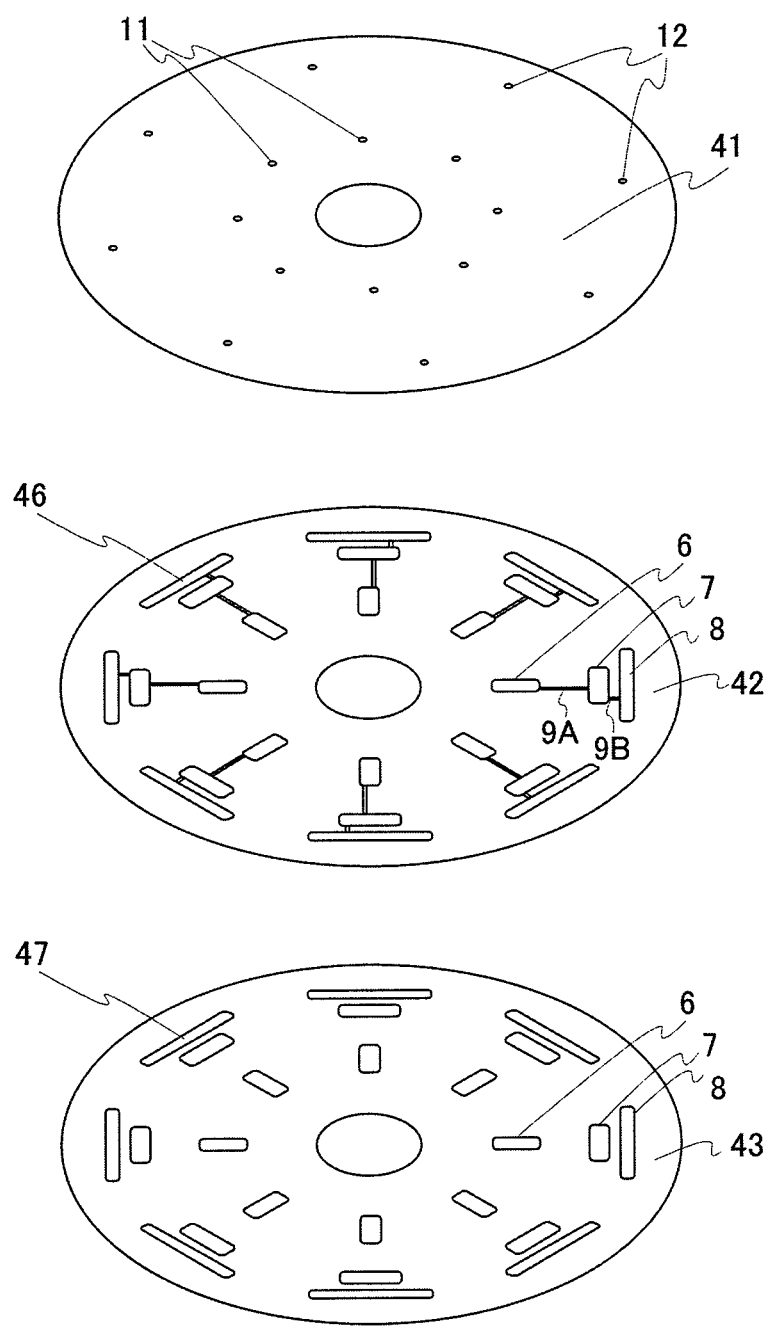
FIG. 5 is an exploded perspective view of a second example of the substrate.

Substrate 2 may have a three-layer structure as shown in FIG. 5. Substrate 2 shown in FIG. 5 includes: upper plate material 41 having injection inlets 11 and air openings 12; flow path plate material 42 having groove holes 46 having shapes corresponding to supply source chambers 6, supply destination chambers 7, final stage chambers 8, and flow paths 9A and 9B; chamber plate material 43 having concave parts 47 corresponding to supply source chamber 6, supply destination chamber 7, and final stage chamber 8.

A Third Example of Layered Structure of Substrate 2

Figure 6:
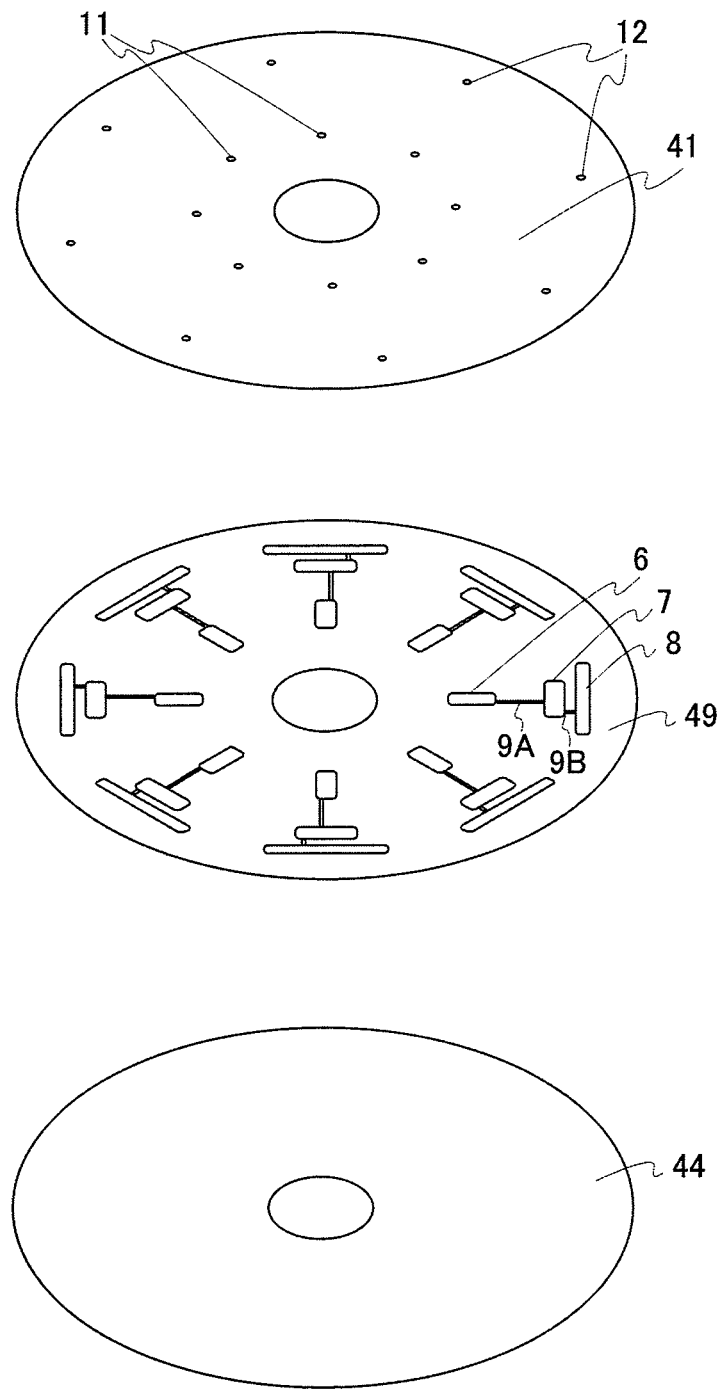
FIG. 6 is an exploded perspective view of a third example of the substrate.

Substrate 2 may have a three-layer structure as shown in FIG. 6. Substrate 2 shown in FIG. 6 includes: upper plate material 41 having injection inlets 11 and air openings 12; flow path plate material 49 that has groove holes 46 corresponding to chambers 6 to 8 and penetrating the flow path plate material in the thickness direction, and has concave parts corresponding to flow paths 9A and 9B; and lower plate material 44 to be bottom parts of supply destination chamber 6 and final stage chamber 8.

A Fourth Example of Layered Structure of Substrate 2

Figure 7:
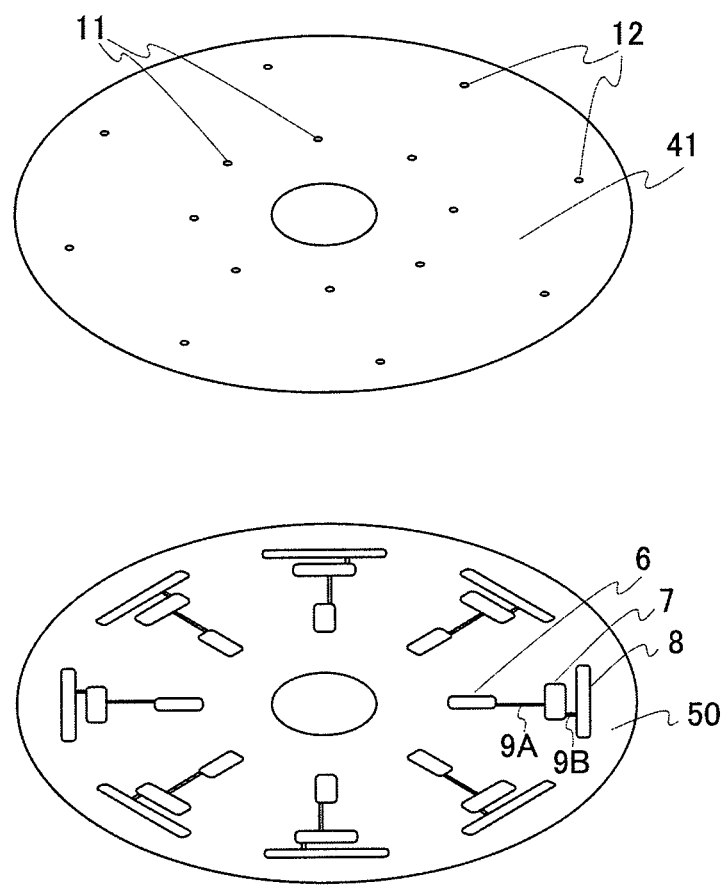
FIG. 7 is an exploded perspective view of a fourth example of the substrate.

Substrate 2 may have a two-layer structure as shown in FIG. 7. Substrate 2 shown in FIG. 7 includes: upper plate material 41 having injection inlets 11 and air openings 12; and lower part plate material 50 having concave parts corresponding to supply source chambers 6, supply destination chambers 7, final stage chambers 8 and flow paths 9A and 9B.

The two-layer structure substrate 2 shown in FIG. 7 can be produced using photolithography, for example. This production process includes: (1) applying photoresist to lower plate material 50 to form flow paths 9A and 9B by lithography (2) forming supply source chamber 6, supply destination chamber 7 and final stage chamber 8, (3) forming injection inlets 11 and air openings 12 in upper plate material 41 and (4) sealing the top part of flow path parts in lower plate material 50 with upper plate material 41.

A specific example will be explained. A negative thick-film photoresist is applied to a glass sheet that is treated clean. A photoresist suitable for the size of the flow paths is selected for use. For example, KMPR1030 (Nippon Kayaku Co., Ltd) is preferable in terms of the thickness of the film and the aspect ratio of flow paths. A spin-coating resist is coated with spin-coater. KMPR 1030 can be coated with the spin-coater comprising steps of pre-rotates ten seconds at 500 rpm, followed by thirty seconds of main rotation at 1000 rpm. By changing the rotation speed of main rotation, it is possible to change the thickness of the film. An example shows that main rotation at 1000 rpm provides a thickness of 57 μm and main rotation at 1070 rpm provides a thickness of 48 μm. After that, pre-bake is carried out for 20 minutes at 95C.°, and exposure is made via a mask on which flow paths and chambers are drawn. The intensity of exposure and duration of exposure may be adequately adjusted depending on the thickness of the film. One example of desirable intensity of exposure is approximately 1700 mJ/cm². PEB (Post Exposure Bake) was performed for 6 minutes at 95C.° and development was carried out, to form flow paths and chamber patterns by photolithography. Next, the chamber parts in lower plate material 50 were formed by cutting or sandblasting. Finally, upper plate material 41, in which injection inlet 11 and air opening 12 are formed, is laminated over lower plate material 50.

[The Method of Transferring a Solution to Chambers in Flow Path Parts]

Figure 8:
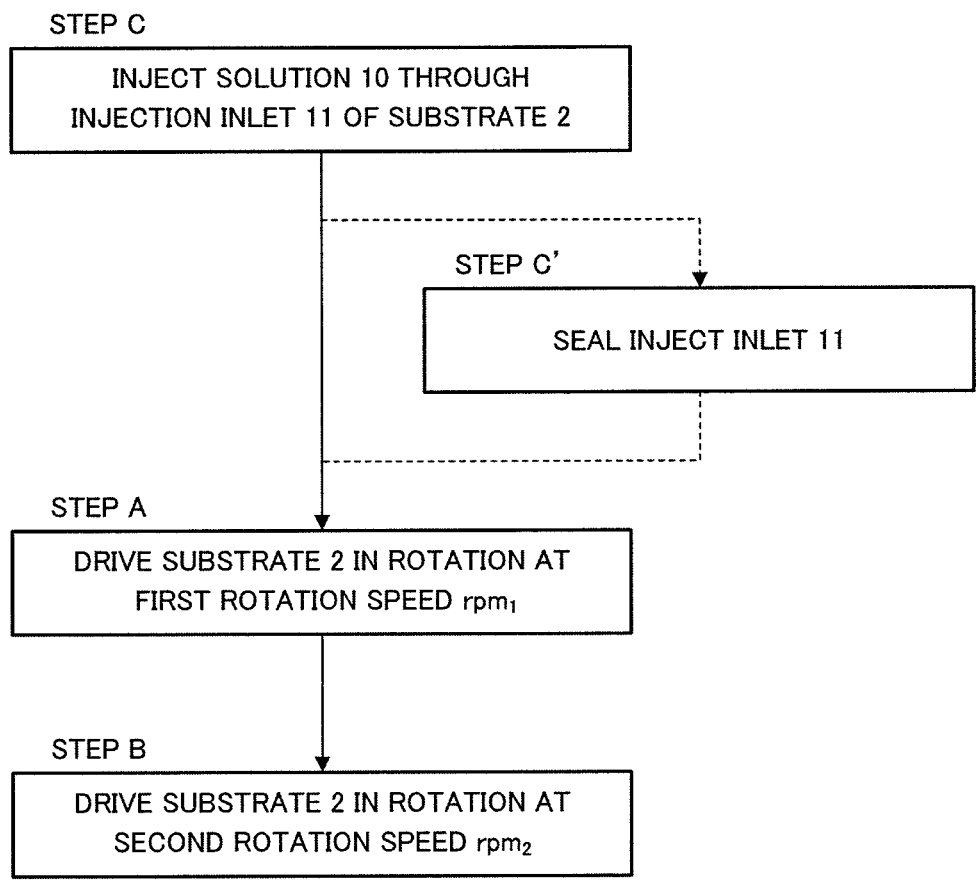
FIG. 8 is a flow chart for stepwise liquid transfer using the liquid transfer apparatus according to Embodiment 1.

The method and mechanism of transferring a solution to chambers in flow path parts in substrate 2 using liquid transfer apparatus 1 will be explained using a flowchart in FIG. 8, and FIG. 9. The liquid transfer method includes the steps of: (A) driving substrate 2 in rotation at the first rotation speed $rpm_1$; and (B) driving substrate 2 in rotation at the second rotation speed $rpm_2$. Prior to step A, (C) injecting solution 10 through injection inlet 11 of substrate 2 to fill in supply source chamber 6 can be included. In step C, the capacity of solution 10 that is injected in supply source chamber 6 is the imaginary chamber volume.

If necessary, injection inlet 11 is sealed (step C') in order to prevent solution 10 from scattering when substrate 2 rotates. By providing injection inlet 11 in a position near rotating shaft 3, solution is hard to scatter due to rotation. Further, scattering is less likely when the opening area of injection inlet 11 is substantially smaller than supply source chamber 6. In contrary, in step C, it is difficult to fill supply source chamber 6 with solution 10. Therefore, by conducting step C', it is possible to both inject solution 10 in supply source chamber 6 reliably and prevent solution 10 from scattering during the rotation of substrate 2.

Figure 9A:
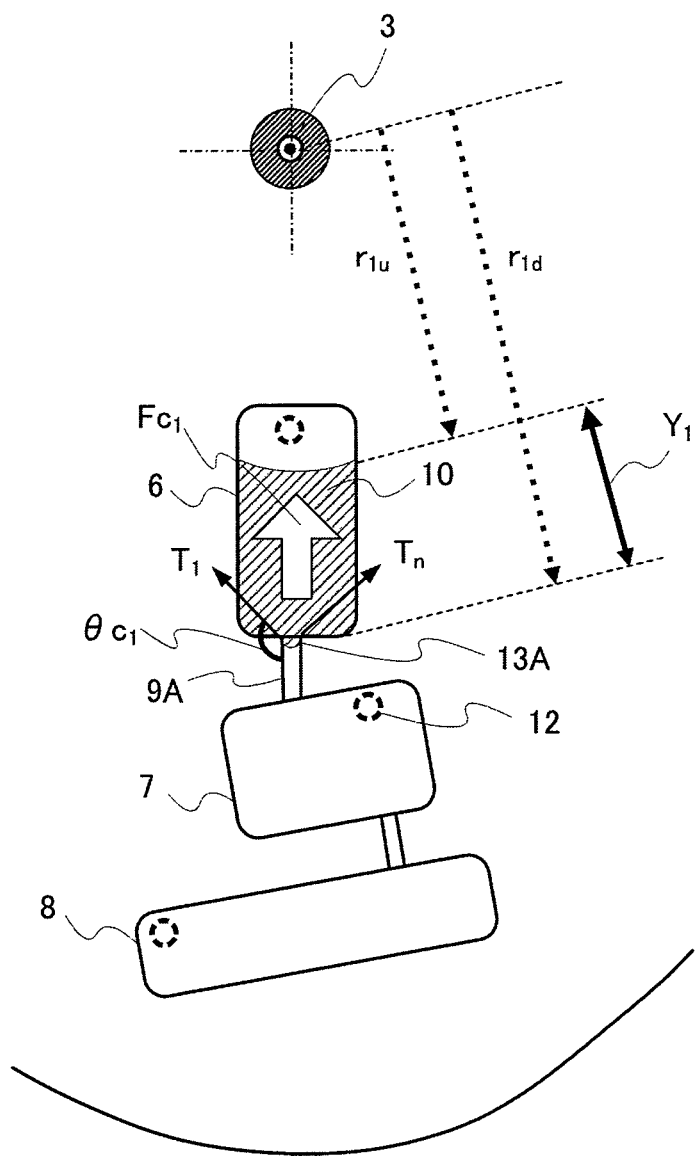
FIG. 9A is a schematic plan view to explain the force that works on the solution during the rotation operation in stepwise liquid transfer in the substrate of the liquid transfer apparatus according to Embodiment 1, showing a state where the solution is retained in the first chamber.
Figure 9B:
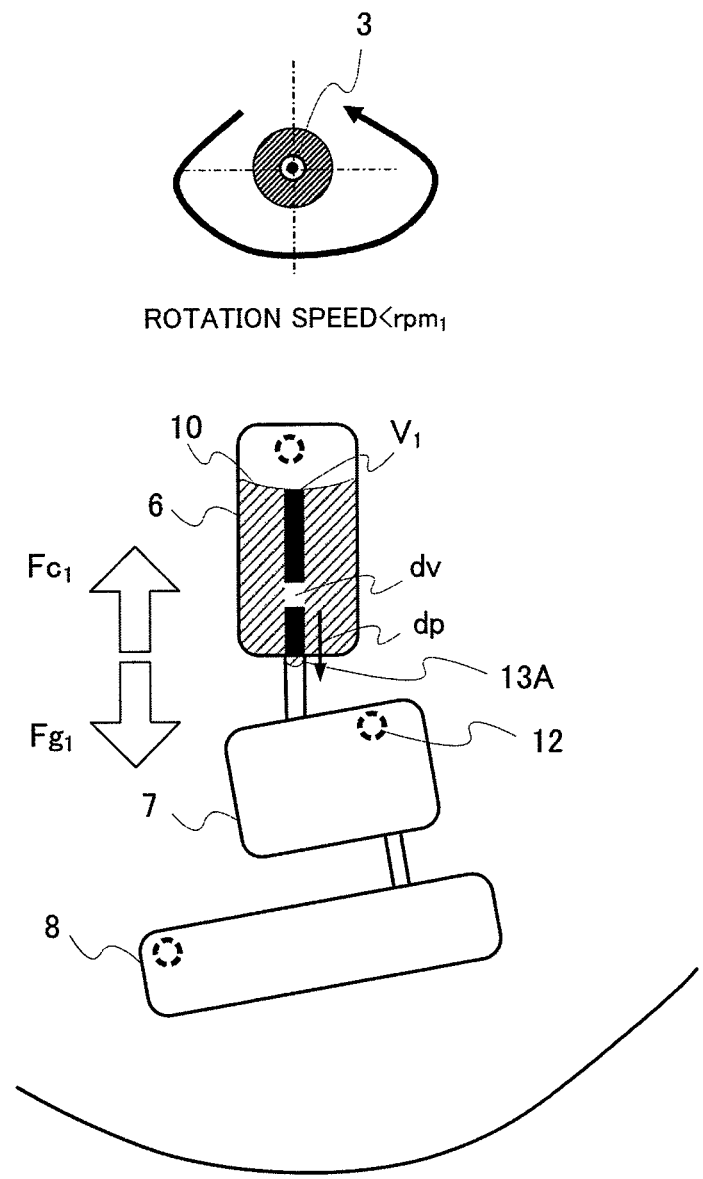
FIG. 9B is a schematic plan view to explain the force that works on the solution in rotational manipulation in stepwise liquid transfer in the substrate of the liquid transfer apparatus according to Embodiment 1, showing a state where the solution flows in the first flow path from the first chamber.

First flow path end part 13A of first flow path 9A connected with supply source chamber 6 in FIGS. 9A and 9B is hydrophobic, and flow path 9A is very thin. The walls of first flow path end part 13A is hydrophobic and is not wet with solution 10, and therefore the contact angle $\theta c_1$ between solution 10 and the walls of flow path is an obtuse angle. For this reason, solution 10 does not flow into flow path 9A by capillary action and the capillary force $Fc_1$ that retains solution 10 in supply source chamber 6. Therefore, solution 10 is retained in first flow path end part 13A by the capillary force $Fc_1$ and does not flow in flow path 9A.

Specifically, the surface tensions $T_1$ to $T_n$ are produced in the interface between the walls of flow path 9A and solution 10. The capillary force $Fc_1$, which is the resultant force of the surface tensions, is produced in the centripetal direction (i.e. the direction from first flow path end part 13A to inside supply source chamber 6). Generally, the magnitude of the capillary force Fc, and the pressure Pc where the capillary force Fc works on flow path end parts 13 are represented by the following equations 1 and 2, respectively, where "T" is the surface tension of water, "θc" is the contact angle of solution with respect to the walls of flow paths, "c" is the contact circumference of flow paths and "S" is the contact area of flow paths.

[1]
$$Fc = T \times \cos\theta c \times c \quad \text{(Equation 1)}$$

[2]
$$Pc = T \times \cos\theta c \times c/S \quad \text{(Equation 2)}$$

The capillary force $Fc_1$ that retains solution 10 on first flow path end part 13A in supply source chamber 6, is based on non-wetting effect and therefore is produced when first flow path end part 13A is hydrophobic. Further, to keep solution 10 on first flow path end part 13A by the capillary force $Fc_1$, flow path 9A needs to be very thin.

As described before, by setting flow path 9A with a width approximately between 4 μm and 2000 μm and with a depth that is shallower than the depths of supply source chamber 6, supply destination chamber 7 and final stage chamber 8, it is possible to reliably retain solution 10 on first connecting end part 13A by the capillary force $Fc_1$.

Substrate 2 drives in rotation at the first rotation speed $rpm_1$ (step A). As shown in FIG. 9B, during the rotation of substrate 2, outward centrifugal force $Fg_1$ in radial directions r works on solution 10 retained on first flow path end part 13A by the capillary force $Fc_1$. The magnitude of the centrifugal force $Fg_1$ is (1) proportional to the volume of solution on which centrifugal force works, (2) proportional to the rotation radius, which gives the distance from the rotating shaft to first flow path end part 13A, and (3) proportional to the square of the rotation speed.

When the centrifugal pressure $Pg_1$ that is produced on first flow path end part 13A by the centrifugal force $Fg_1$ exceeds the capillary pressure $Pc_1$ that is produced on first flow path end part 13A by the capillary force $Fc_1$, solution 10 in first flow path end part 13A intrudes in flow path 9A. In cases where the centrifugal pressure $Pg_1$ is smaller than the capillary pressure $Pc_1$, solution 10 is retained on first flow path end part 13A even when the centrifugal force $Fg_1$ works.

As described before, the magnitude of centrifugal force Fg is proportional to the square of rotation speed. The rotation speed at which the centrifugal pressure $Pg_1$ exceeds the capillary pressure $Pc_1$ is "the first rotation speed $rpm_1$." That is, by driving substrate 2 in rotation at the first rotation speed $rpm_1$, it is possible to let solution 10 in first chamber 6 flow in flow path 9A. The direction rotation may be clockwise or counterclockwise.

The time and acceleration to reach the first rotation speed $rpm_1$ from a stop mode are set arbitrarily. Solution 10 is kept retaining in first chamber 6 while substrate 2 drives in rotation at lower rotation speed than the first rotation speed $rpm_1$. Then, when solution 10 is blood, substrate 2 may drive in rotation at lower rotation speed than the first rotation speed $rpm_1$ for a predetermined period, to carry out centrifugal separation of the blood cells contained in blood.

In cases where the entirety of flow path 9A except for first flow path end 13A, first chamber 6 and second chamber 7 are hydrophilic, when retaining solution 10 is released from being retained in first flow path end part 13A by the centrifugal pressure $Pg_1$, solution 10 in first chamber 6 flows into second chamber 7 through flow path 9A by humidifying effect or capillary action. At this time, the air in flow path 9A and second chamber 7 is exhausted from substrate 2 via air opening 12. By capillary action, solution 10 spreads to the corners of flow path 9A and second chamber 7, so that solution 10 can flow in second chamber 7 reliably and quantitatively.

Figure 9C:
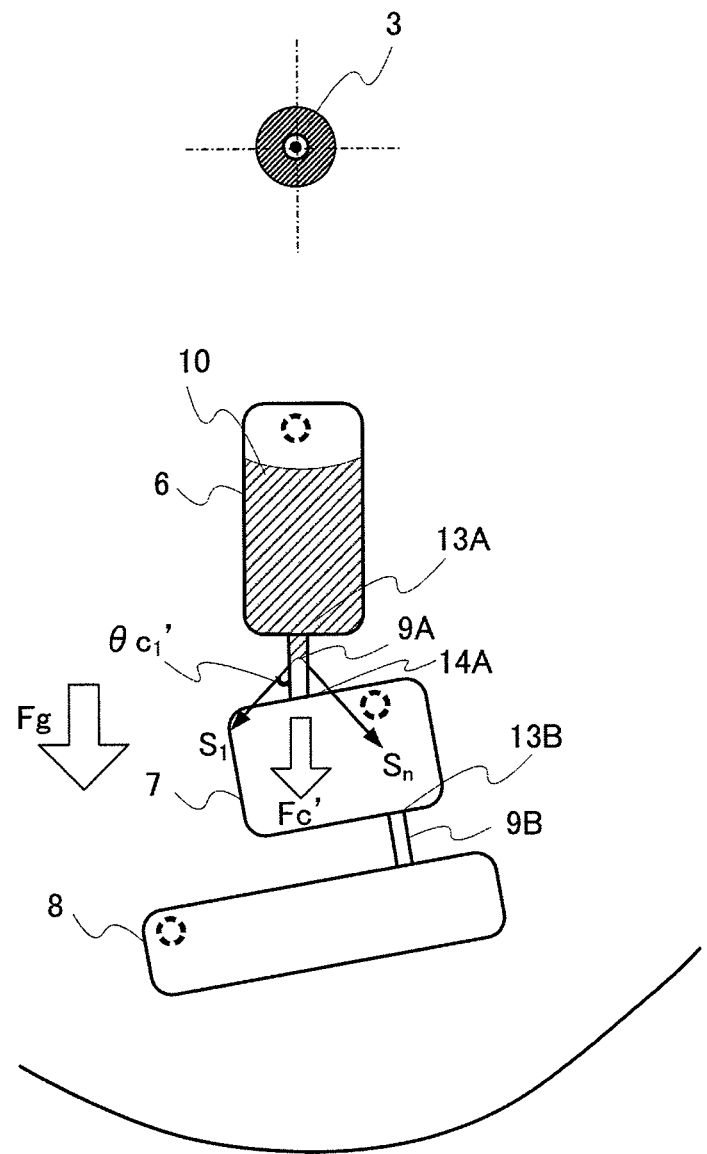
FIG. 9C is a schematic plan view to explain the force that works on the solution during the rotation operation in stepwise liquid transfer in the substrate of the liquid transfer apparatus according to Embodiment 1, showing a state where the solution flows in the first flow path.
Figure 9D:
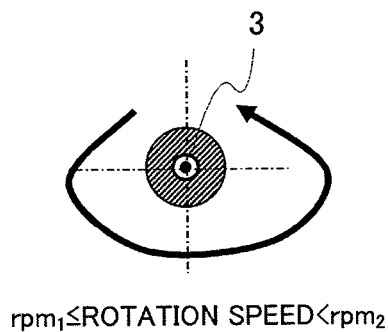
FIG. 9D is a schematic plan view to explain the force that works on the solution during the rotation operation in stepwise liquid transfer in the substrate of the liquid transfer apparatus according to Embodiment 1, showing a state where the solution flows into the second chamber.
Figure 9D:
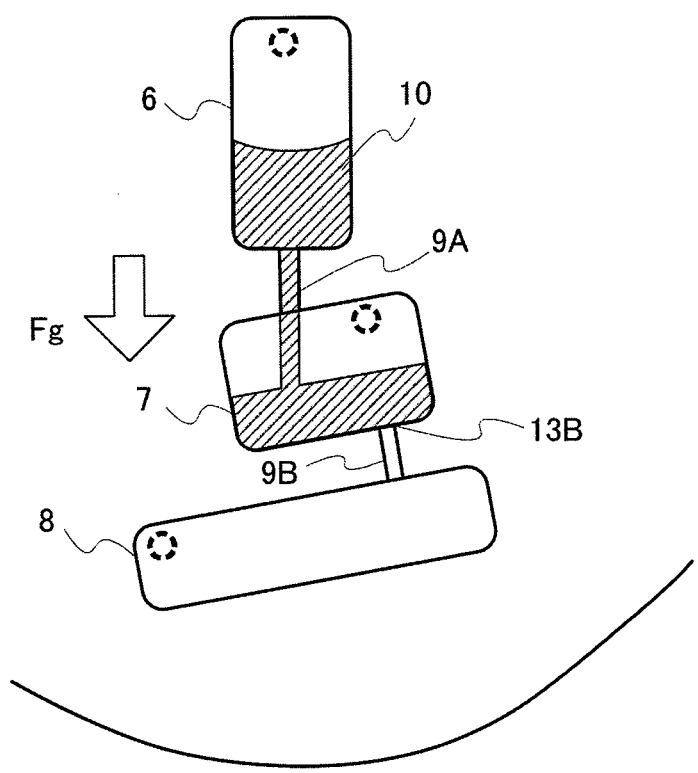

Capillary action will be explained using FIG. 9C. When the walls of first flow path 9A, which is hydrophilic, becomes wet, the contact angle $\theta c_1$ between the solution and the walls of the flow path becomes an acute angle. Surface tensions $S_1$ to $S_n$ are produced in the interface between the walls of the flow path and solution 10. The capillary force Fc', which is the resultant force of the surface tensions, is produced in the centripetal direction. Therefore, the capillary force Fc' works on solution 10 which have been flown in flow path 9A from first flow path end part 13A, to fill flow path 9A with solution 10. The magnitude of the capillary force Fc' is represented similar to above equation 1.

Figure 9E:
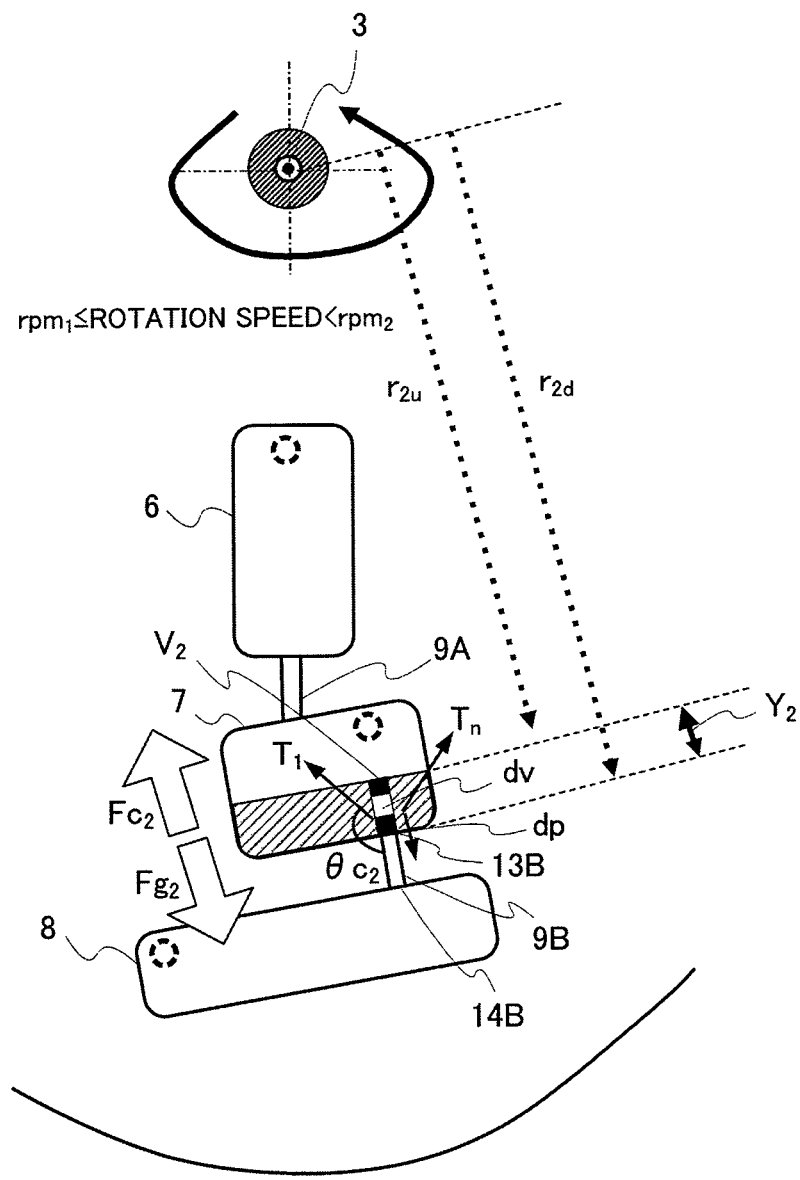
FIG. 9E is a schematic plan view to explain the force that works on the solution during the rotation operation in stepwise liquid transfer in the substrate of the liquid transfer apparatus according to Embodiment 1, showing a state where the solution is retained in the second chamber.

Next, solution 10, which has flown in second chamber 7 from second flow path end part 14A of flow path 9A, continues receiving the centrifugal force $Fg_1$. Third flow path end part 13B is not on the straight line connecting rotating shaft 3 and second flow path end part 14A, and therefore solution 10 encounters the side wall on the outer periphery side of second chamber 7. Then, as described before, third flow path end part 13B of flow path 9B connected with second chamber 7 is hydrophobic, and flow path 9B is very thin, so that solution 10 in third flow path end part 13B receives the capillary force $Fc_2$ generated by surface tension (FIG. 9E).

As described before, centrifugal force Fg' increases in proportion to the rotation radius as shown in equation 3. The symbol "ρ" is the density of solution, symbol "V" is the volume of solution centrifugal force Fg works on, symbol "r" is the rotation radius and symbol "ω" is the angular velocity.

[3]
$$Fg' = \rho V \times r \times \omega^2 \quad \text{(Equation 3)}$$

The rotation speed rpm and the angular velocity ω hold the relationship of equation 4.

[4]
$$rpm = \frac{\omega}{2\pi} \times 60 \quad \text{(Equation 4)}$$

Second chamber 7 is placed outer periphery side more than first chamber 6, and the distance from rotating shaft 3 to third flow path end part 13B (rotation radius) $r_{2d}$ is longer than the distance from the rotating shaft 3 to first flow path end part 13A (rotation radius) $r_{1d}$ (see FIGS. 9A and 9E). Therefore, as derived from equation 3, the centrifugal force $Fg_2$ that works on third flow path end part 13B of second chamber 7 is greater than the centrifugal force $Fg_1$ that works on first flow path end part 13A of first chamber 6, if other conditions (i.e. the density of solution, the volume of solution subjected to force and the angular velocity) are the same.

Figure 9F:
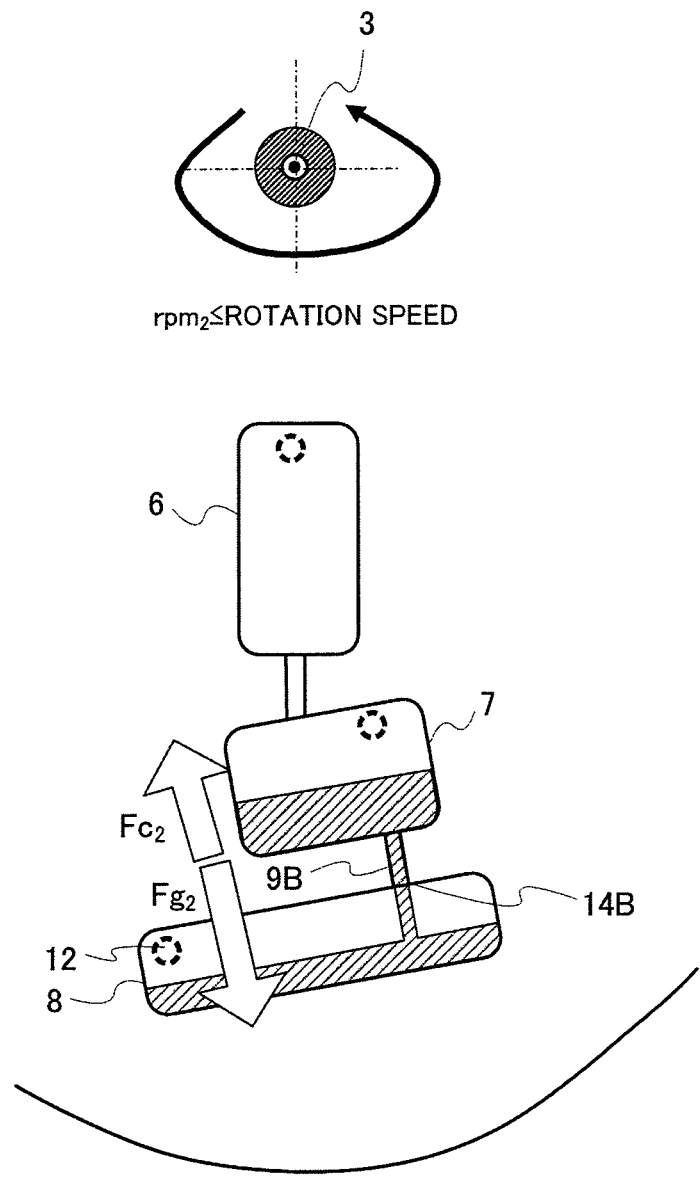
FIG. 9F is a schematic plan view to explain the force that works on the solution during the rotation operation in stepwise liquid transfer in the substrate of the liquid transfer apparatus according to Embodiment 1, showing a state where the solution flows in the third chamber.

When the cross-sectional area of second flow path 9B and the cross-sectional area of the first flow path 9A are equal and the capillary force $Fc_2$ that is produced on the third flow path end part 13B and the capillary force $Fc_1$ that is produced on the first flow path end part 13A are equal, solution 10 which flows in second chamber 7 by the rotation drive of substrate 2 at the first rotation speed $rpm_1$, flows into flow path 9B and then flows into final stage chamber 8 without staying in second chamber 7 based on the balance between capillary force and centrifugal force (FIG. 9F).

Then, by making width 22 of second chamber 7 (see FIG. 3) longer than width 21 of first chamber (see FIG. 3), volume V of the solution on which centrifugal force works is adjusted.

First, the centrifugal pressure $Pg_1$ that works on first flow path end part 13A of first chamber 6 is exactly found. FIGS. 9A to 9D show states of the solution where first chamber 6 is filled with solution 10 having the imaginary chamber volume and where substrate 2 drives in rotation. All solution 10 receives the centrifugal force $Fg_1$ and moves to the outer periphery side of first chamber 6 (FIG. 9A) with the rotation. The length from first flow path end part 13A to the solution surface in a plan view is "first imaginary chamber length $Y_1$" (FIG. 9A). The volume of solution 10 on first flow path end part 13A, which contributes to the centrifugal pressure $Pg_1$, represents the "first contribution volume $V_1$" (FIG. 9B). "The first contribution volume $V_1$" is shown as a rectangular parallelepiped in which the cross-sectional area of the first flow path end part 13A is the bottom and in which the first imaginary chamber length $Y_1$ is the height.

The centrifugal pressure $Pg_1$ is represented as equation 5 with the micro-volume dv and the micro-centrifugal pressure dp the micro-volume dv produces, shown in FIG. 9B. By integrating equation 5 from the rotation radius $r_{1u}$ to the rotation radius $r_{1d}$, the centrifugal pressure Pg1 is calculated (FIG. 9A).

[5]

$$P_{g1} = \int_{r_{1u}}^{r_{1d}} dp \quad \text{(Equation 5)}$$

$$P_{g1} = \int_{r_{1u}}^{r_{1d}} \rho \omega^2 \, dr \quad \text{(Equation 6)}$$

$$= \frac{\rho \omega_1^2}{2} Y_1 (2r_{1d} - Y_1) \quad \text{(Equation 7)}$$

$r_{1d} \gg Y_1$, and therefore $2r_{1d} - Y_1$ may be an approximate of $2r_{1d}$. That is, the centrifugal pressure $Pg_1$ is proportional to the imaginary chamber length $Y_1$.

The centrifugal pressure $Pg_2$ can be obtained in the same way (see FIG. 9E). The centrifugal pressure $Pg_2$ that the second contribution volume $V_2$ causes is represented as equation 8, by integrating from the rotation radius $r_{1u}$ to the rotation radius $r_{1d}$, with the micro-volume dv and the microcentrifugal pressure dp the micro-volume dv produces shown in FIG. 9E.

[6]

$$P_{g2} = \frac{\rho \omega_2^2}{2} Y_2 (2r_{2d} - Y_2) \quad \text{(Equation 8)}$$

$r_{2d} \gg Y_2$, and therefore, $2r_{2d} - Y_2$ can be an approximate of $2r_{2d}$. That is, the centrifugal pressure $Pg_2$ is proportional to the imaginary chamber length $Y_2$.

The cross-sectional area of first flow path end part 13A and the cross-sectional area of the third flow path end part 13B are equal, and, when the capillary pressure $Pc_1$ and capillary pressure $Pc_2$ that are produced on the flow path end parts are equal, $Pg_1 \geq Pg_2$, and it is necessary to fulfill $\omega_1 < \omega_2$. When $Pg_1 = Pg_2$, the imaginary chamber lengths $Y_1$ and $Y_2$ require the relationship of equation 9 to fulfill the relationship of $\omega_1 < \pm \omega_2$.

[7]

$$Y_2 (2r_{2d} - Y_2) < Y_1 (2r_{1d} - Y_1) \quad \text{(Equation 9)}$$

As described above, on the assumption that $r_{1d} \gg Y_1$ and $r_{2d} \gg Y_2$, the relationship in the chamber lengths $Y_1$ and $Y_2$ shown in equation 9 is simplified with equation 10.

[8]

$$Y_2 < \frac{r_{1d}}{r_{2d}} Y_1 \quad \text{(Equation 10)}$$

When the relationship between first chamber 6 and second chamber 7 fulfills equation 9 or 10, solution 10 having flown from first flow path 9A to the second chamber by rotating the substrate at first rotation speed $rpm_1$, cannot flow into second flow path 9B, depending on the first rotation speed $rpm_1$.

After a predetermined duration following step A, substrate 2 is rotated at the second rotation speed $rpm_2$ or more (step B). The second rotation speed $rpm_2$ is higher than the first rotation speed $rpm_1$. The second centrifugal force $Fg_2$ upon which the second rotation speed $rpm_2$ is produced on substrate 2 is greater than $Fg_1$ as derived from equation 3. That is, the centrifugal pressure $Pg_2$ that is produced on third flow path end part 13B by centrifugal force $Fg_2$ cancels out the capillary pressure Pc2 that is produced on third flow path part 13B by the capillary force Fc2. As a result, solution 10 of third flow path end part 13B flows in flow path 9B.

That is, by driving substrate 2 in rotation at the second rotation speed $rpm_2$, it is possible to let solution 10 in second chamber 7 flow in flow path 9B. The direction of rotation may be clockwise direction $R_1$ or counterclockwise direction $R_2$. The time and acceleration to reach the second rotation speed $rpm_2$ are set arbitrarily. Solution 10 is retained in second chamber 7 as long as substrate 2 drives in rotation at the second rotation speed $rpm_2$ or lower. Then, in cases where solution 10 is an aqueous solution containing chemical substances, and where reagents that can react with the chemical substances are supported in second chamber 7 in advance, the reagents can react with the aqueous solution containing chemical substances in a predetermined duration in second chamber 7.

Here, the imaginary chamber lengths $Y_1$ and $Y_2$ shown in equation 9 are preferably between 0.1 mm and 5 mm. It is difficult to place a solution in chambers such that the imaginary chamber lengths are 0.1 mm or less, due to the cohesive force of the solution. Meanwhile, the diameter of the normal substrate 2 is approximately 10 mm, and therefore, if the imaginary chamber length is made 5 mm or more, there may not be room to arrange supply destination chamber 8 in the substrate.

Taking into consideration of the variations of physical properties in a biological sample described before, it is desirable to estimate the second imaginary chamber length $Y_2$ shown in equation 10 to be approximately 0.3 mm longer and determine the width and depth of the chamber, so as to fulfill the relationship of equation 10. By this design, it is possible to make the difference between the first rotation speed and the second rotation speed 200 rpm or more, thereby more reliably realizing stepwise liquid transfer.

To set up an adequate difference between the first rotation speed and the second rotation speed, it is preferable to set the ratio between the first imaginary chamber length $Y_1$ and the second imaginary chamber length $Y_2$, $Y_1/Y_2$, in 1.6 or more.

In cases where the entirety of flow path 9B except for third flow path end 13B, second chamber 7 and third chamber 8 are hydrophilic, solution 10 in second chamber 7 flows into third chamber 8 through flow path 9B by humidifying effect or capillary action upon releasing solution 10 from being retained in third flow path end part 13B. The air in flow path 9B and third chamber 8 is exhausted from substrate 2 via air opening 12. By capillary action, solution 10 spreads to corners of flow path 9B and third chamber 8, so that solution 10 can flow in third chamber 8 reliably and quantitatively.

As described above, by driving substrate 2 in rotation at the first rotation speed $rpm_1$, it is possible to transfer solution 10 from first chamber 6 to second chamber 7 selectively; and then, by driving substrate 2 in rotation at the second rotation speed $rpm_2$, it is possible to transfer solution 10 from second chamber 7 to third chamber 8 selectively. By this means, stepwise liquid transfer is realized.

Liquid transfer apparatus 1 of the present invention provides various advantages as listed below. First, by changing the shapes of miniature chambers according to the distance from the axis of rotation, liquid is transferred stepwise through microchambers, according to the rotation speed of the substrate. Consequently, the cross sectional areas and shapes of micro-flow paths that connect between microchambers do not need to vary, so that the flow paths can be designed to be same width or same depth. This configuration makes it possible to produce micro-flow paths easily, and therefore the making process does not involve a load.

Secondly, the volume of solution that generates centrifugal force which works on flow path end parts and which opposes capillary force, is reduced in chamber on the outer periphery side. Centrifugal force increases according to the distance from the axis of rotation. Therefore, the rotation speed required to generate centrifugal force exceeding capillary force increases, when the position where the solution is retained is close the outer periphery side. By this means, it is possible to realize liquid transfer through microchambers, according to the rotation speed of the substrate. Therefore, it is possible to improve the feasibility of manufacturing the liquid transfer apparatus, and give various functions to liquid transfer mechanism. Further, liquid transfer is realized by the apparatus even when the volume of solution to be transferred is little.

Embodiment 2

Figure 10:
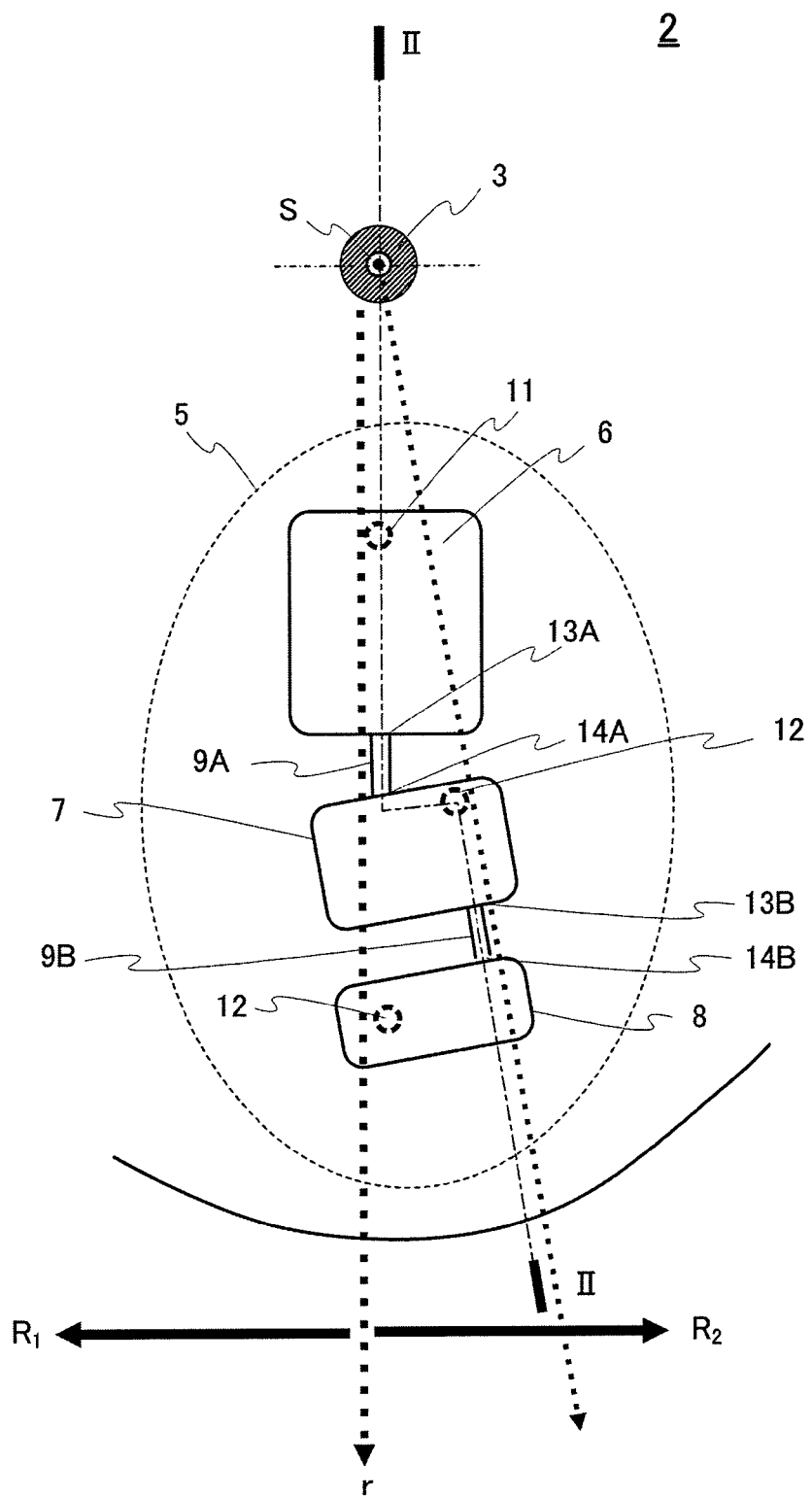
FIG. 10 is a partial expanded plan view of the substrate according to Embodiment 2.

Liquid transfer apparatus 1 according to Embodiment 2 includes the rotation drive apparatus shown in FIG. 1 and substrate 2 shown in FIGS. 10 and 11. These figures will be used in the following description.

Substrate 2 of Embodiment 2 differs from substrate 2 of Embodiment 1 in flow path parts 5. To summarize the difference, with Embodiment 1 the relationships of imaginary chamber lengths shown in equation 9 or 10 are fulfilled by changing the width of chambers, so that stepwise liquid transfer is realized. Meanwhile, with Embodiment 2 the depths of chambers vary.

Figure 11A:
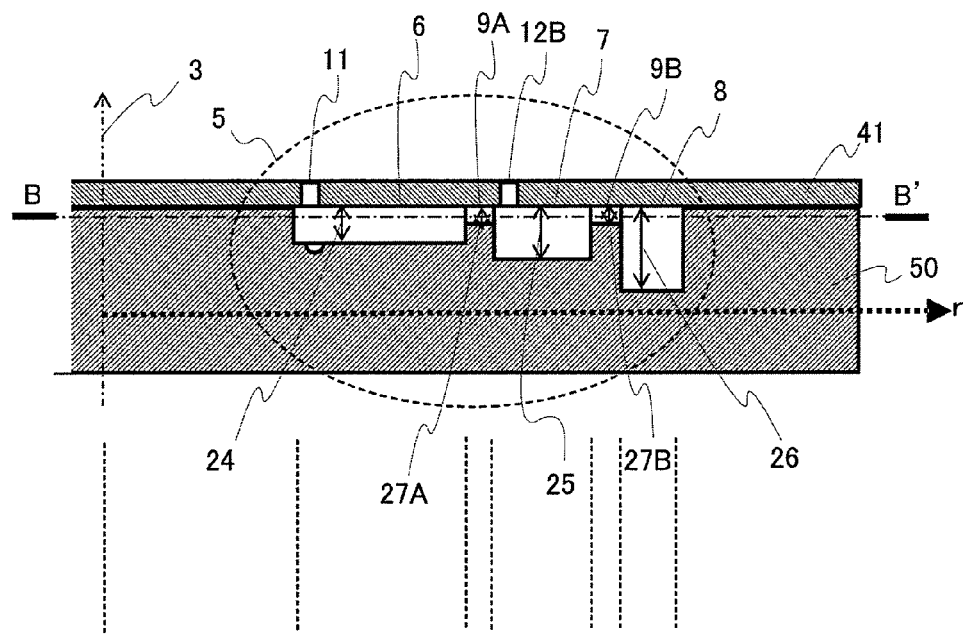
FIG. 11 is a partial cross-sectional view (FIG. 11A) along I-I line in FIG. 10, and a corresponding plan view (FIG. 11B)
Figure 11B:
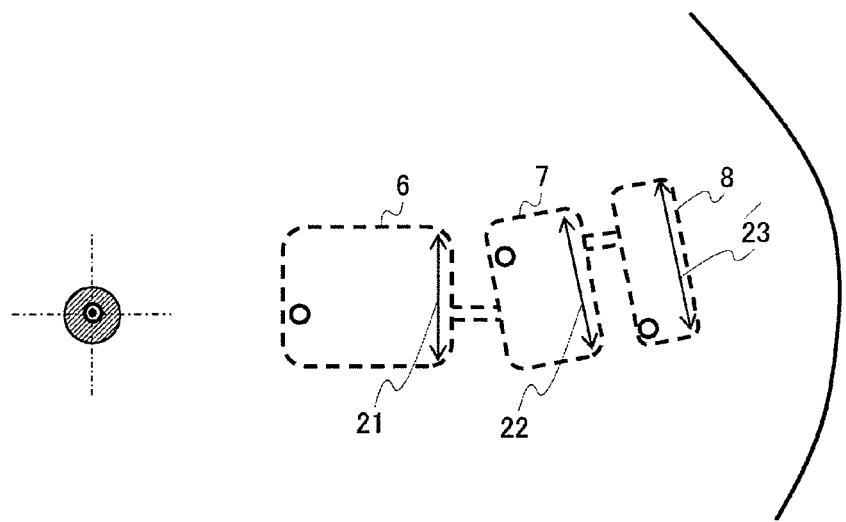

Flow path part 5 of substrate 2 of Embodiment 2 will be explained using FIGS. 10 and 11. In a plan view, width 21 of first chamber 6 and width 22 of second chamber 7 are approximately equal (FIG. 11B). Meanwhile, depth 24 of first chamber 6 is shallower than depth 25 of second chamber 7 (FIG. 11A).

The first capillary force $Fc_1$ works on solution 10 provided in first chamber 6 through injection inlet 11 in first flow path end part 13A, to prevents solution 10 from flowing in first flow path 9A. When substrate 2 drives in rotation, centrifugal force $Fg_1$ is produced along the centrifugal direction of radial direction r. When the rotation speed reaches first rotation speed $rpm_1$, the centrifugal pressure $Pg_1$ that works on first flow path end part 13A generated by the first contribution volume $v_1$, exceeds the capillary pressure $Pc_1$ generated by the capillary force $Fc_1$. Then, solution 10 flows in flow path 9A and flows in second chamber 7.

Depth 24 of first chamber 6 is shallower than depth 25 of second chamber 7, so that second imaginary chamber length $Y_2$, which is the length where solution 10 fills second chamber 7, is shorter than the first imaginary chamber length $Y_1$. If the relationship between the first imaginary chamber length $Y_1$ and the second imaginary chamber length $Y_2$ in substrate 2 in Embodiment 2 fulfills equation 9 or 10, the centrifugal pressure $Pg_2$ produced by the second contribution volume $V_2$ is less than the second capillary pressure $Pc_2$ that works on third flow path end part 13B. Therefore, solution 10 can stay in second chamber 7.

After that, substrate 2 drives in rotation at the second rotation speed $rpm_2$ higher than the first rotation speed $rpm_1$ (step B). Second centrifugal pressure $Fg_2$ produced by second rotation speed $rpm_2$ is represented by equation 8. Second centrifugal pressure $Fg_2$ exceeds the second capillary pressure $Pc_2$ for the first time, so that solution 10 in second chamber 7 flows in flow path 9B and then flows in third chamber 8.

As described above, substrate 2 of Embodiment 2 drives in rotation at the first rotation speed $rpm_1$, so that it is possible to transfer solution 10 from first chamber 6 to second chamber 7 selectively. Further, substrate 2 drives in rotation at the second rotation speed $rpm_2$, so that it is possible to transfer solution 10 from second chamber 7 to third chamber 8 selectively. By this means, stepwise liquid transfer is realized.

Substrate 2 of Embodiment 2 needs not adjust the width of chambers as substrate 2 of Embodiment 1, so that it is possible to reduce the area for forming flow path part 5 in a plan view. Therefore, substrate 2 provides an advantage of integrating a plurality of flow path parts 5 with density in substrate 2, to lower the production cost.

Depth 26 of third chamber 8 is shallower than depth 25 of second chamber 7. Depth 26 of third chamber 8 may be set on arbitrary basis, as long as chamber 8 can accommodate solution of imaginary chamber volume 15 such that the solution does not leak out. Further, the number of third chambers 8 is not limited to one, and, two or more third chambers 8 may be placed so as to communicate with flow paths. Further, chamber widths (see Embodiment 1) and chamber depths (see Embodiment 2) may be combined to be adjusted.

Embodiment 3

Figure 12:
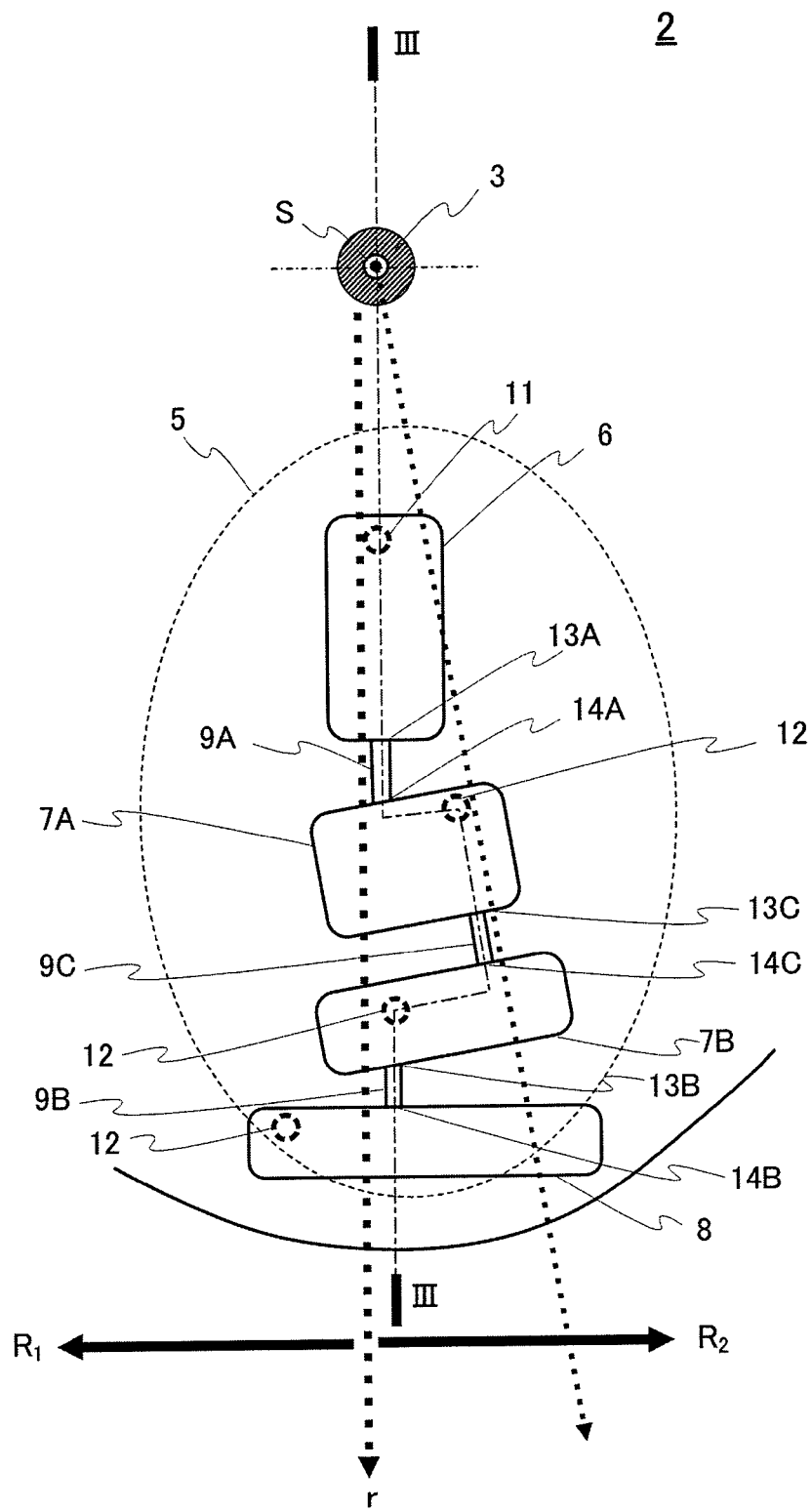
FIG. 12 is a partial expanded plan view of the substrate according to Embodiment 3.
Figure 13A:
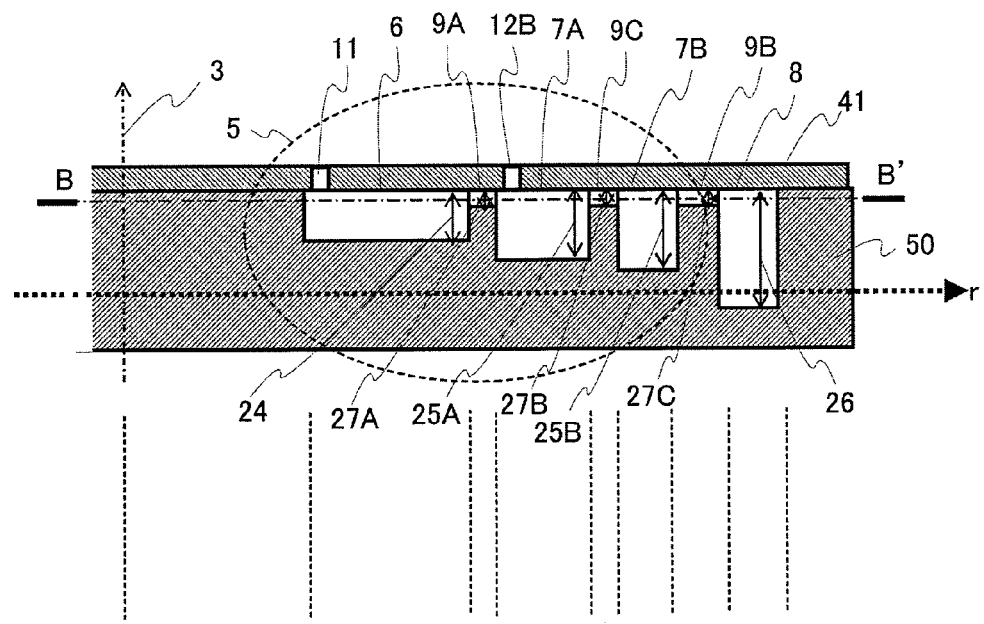
FIG. 13 is a partial cross-sectional view (FIG. 13A) along I-I line in FIG. 12, and a corresponding plan view (FIG. 13B)
Figure 13B:
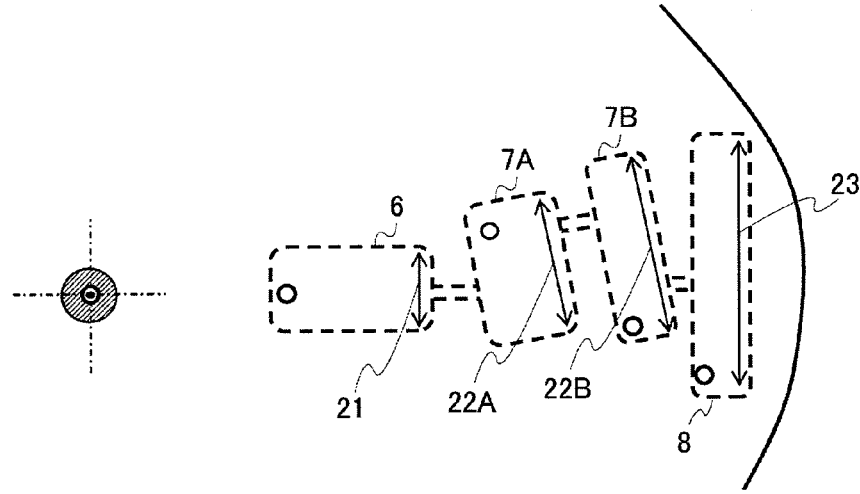

Liquid transfer apparatus 1 according to Embodiment 3 includes the rotation drive apparatus shown in FIG. 1 and substrate 2 shown in FIGS. 12 and 13. These figures will be used in the following description. Substrate 2 of Embodiment 3 differs from substrate 2 of Embodiment 1 in the number of chambers in that flow path part 5. That is, flow path 5 has a plurality of second chambers (second chamber 7A and second chamber 7B). Second chamber 7A is placed on the inner periphery side and second chamber 7B is placed on the outer periphery side. The second chambers communicate each other via flow path 9C and are arranged in series in the radial direction.

As shown in FIG. 12, second chamber 7A and second chamber 7B communicate each other through flow path 9C, which has fifth flow path end part 13C and sixth flow path end part 14C. Width 22A of second chamber 7A is narrower than width 22B of second chamber 7B in a plan view. Also, as shown in FIG. 13A, depth 25A of second chamber 7A is shallower than depth 25B of second chamber 7B.

Figure 14:
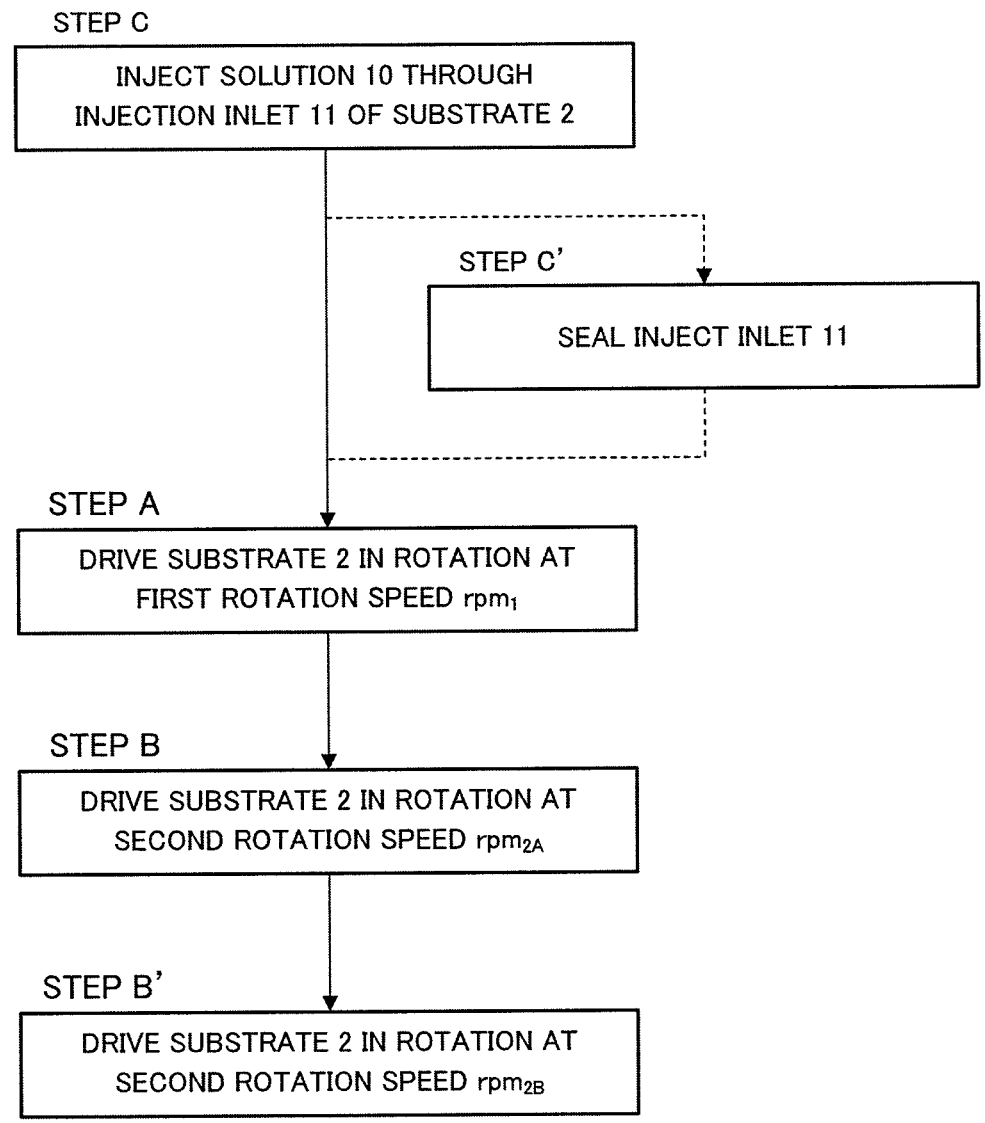
FIG. 14 is a flow chart for transfer liquid stepwise using the liquid transfer apparatus according to Embodiment 3.

FIG. 14 is a flow chart for carrying out liquid transfer using substrate 2 of Embodiment 3. The first capillary force $Fc_1$ works on solution 10 injected in first chamber 6 through injection inlet 11 in first flow path end part 13A, to prevent solution 10 from flowing in flow path 9A. When substrate 2 drives in rotation, centrifugal force $Fg_1$ is produced in the centrifugal direction of radial direction r. When the rotation speed reaches first rotation speed $rpm_1$, the centrifugal pressure $Pg_1$ by the contribution volume $V_1$ of solution 10 which works on first flow path end part 13A exceeds the capillary pressure $Pc_1$ by the capillary force $Fc_1$, and then solution 10 flows in flow path 9A and flows in second chamber 7A.

Width 22A of second chamber 7A is wider than width 21 of first chamber 7, so that imaginary chamber length $Y_{2A}$, which is the length where solution 10 fills second chamber 7A, is narrower than the first imaginary chamber length $Y_1$. If the relationship between the first imaginary chamber length $Y_1$ and the second imaginary chamber length $Y_{2A}$ in substrate 2 of Embodiment 3 fulfills equation 9 or 10, the centrifugal pressure $Pg_{2A}$ produced by the second contribution volume $V_{2A}$ is less than the capillary pressure $Pc_{2A}$ that works on fifth flow path end part 13C. Therefore, solution 10 flowing in second chamber 7A can stay in second chamber 7A.

Next, substrate 2 drives in rotation at the second rotation speed $rpm_{2A}$ higher than the first rotation speed $rpm_1$ (step B). Second centrifugal force $Fg_{2A}$ produced by second rotation speed $rpm_{2A}$ is represented by equation 8. Second centrifugal force $Fg_{2A}$ exceeds the second capillary pressure $Pc_{2A}$ for the first time. Therefore, solution 10 in second chamber 7A flows into flow path 9C and reaches second chamber 7B.

Width 22B of second chamber 7B is wider than width 22A of second chamber 7A, so that imaginary chamber length $Y_{2B}$, on which second chamber 7B is provided with solution 10, is narrower than the second imaginary chamber length $Y_{2A}$. If the relationship between the imaginary chamber length $Y_{2A}$ and the imaginary chamber length $Y_{2B}$ in substrate 2 in Embodiment 3 fulfills equation 9 or 10, the centrifugal pressure $Pg_{2B}$ produced by the second contribution volume $V_{2B}$ does not exceed the capillary pressure $Pc_{2B}$ that works on third flow path end part 13B.

Next, substrate 2 drives in rotation at the second rotation speed $rpm_{2B}$ higher than the rotation speed $rpm_{2A}$ (step B'). Second centrifugal force $Fg_{2B}$ produced by the rotation speed $rpm_{2B}$ is represented by equation 8. Second centrifugal force $Fg_{2B}$ exceeds the second capillary pressure $Pc_{2B}$ for the first time. Therefore, solution 10 in second chamber 7B flows into flow path 9B and reaches third chamber 8.

As described above, it is possible to transfer solution 10 from first chamber 6 to second chamber 7 selectively by driving substrate 2 in rotation at the first rotation speed $rpm_1$; it is possible to transfer solution 10 from second chamber 7A to second chamber 7B selectively by driving substrate 2 in rotation at the second rotation speed $rpm_{2A}$; and, it is possible to transfer solution 10 from second chamber 7B to third chamber 8 selectively by driving substrate 2 in rotation at the second rotation speed $rpm_{2B}$. In this way, it is possible to transfer a solution in three stages.

The number of second chambers to place in substrate 2 of Embodiment 3 increases, so that the number of stages in liquid transfer increases. Consequently, the number of steps conducted in substrate 2 (e.g. mixing solutions and reactions of chemical substances) can increase, thereby carrying out complicated process easily.

Embodiment 4

Figure 15:
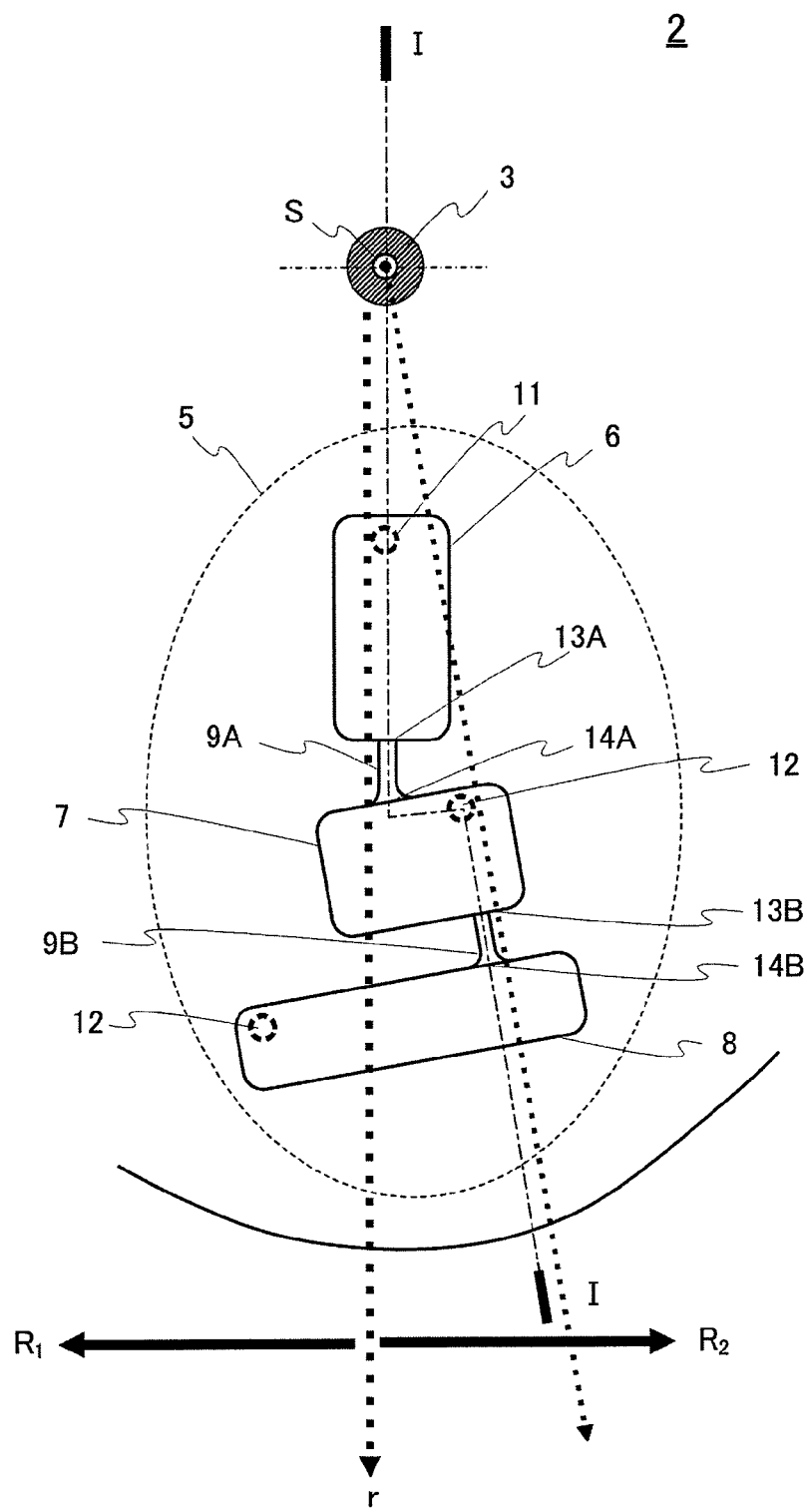
FIG. 15 is a partial expanded plan view of the substrate according to Embodiment 4.

Liquid transfer apparatus 1 according to Embodiment 4 includes the rotation drive apparatus shown in FIG. 1 and substrate 2 shown in FIG. 15. These figures will be used in the following description.

Substrate 2 of Embodiment 4 differs from substrate 2 of Embodiment 1 in the shape of flow paths 9A and 9B in flow path part 5. To summarize this difference, the cross-sectional area of the inlets (13A and 13B) of the flow paths (9A and 9B) connected with inner chambers are different from the cross-sectional area of the outlets (14A and 14B) of the flow paths connected with the outer chambers. Specifically, the width and depth of the flow paths change near the outlet end parts.

As shown in FIG. 15, the cross-sectional areas of the outlets gradually increase near second flow path part end 14A which is outlet end part of first flow path 9A, and near fourth flow path part end 14B which is outlet end part of second flow path 9B. The cross-sectional area becomes maximum in connecting points of second chamber 7 and third chamber 8, respectively. FIG. 15 shows an example where the cross-sectional areas of the flow paths gradually increase near connecting points with the chambers such that the flow paths have round corners. Certainly, the shapes to increase the cross-sectional areas are not limited to this, and, for example, the depth of flow paths may vary. The amount and rate of increase of cross-sectional areas are not limited.

Meanwhile, the cross-sectional area of the inlets are constant near first flow path end part 13A which is inlet end part of the first flow path, and near third flow path end part 13B which is inlet end part of second flow path.

One example is that, when the depth and width of first flow path 9A except for the vicinity of second flow path end part 14A are 0.04 mm and 0.2 mm, respectively, the depth and width of second flow path end part 14A can be 0.04 mm (unchanged) and 0.6 mm, respectively. To be more specific, the cross-sectional area having round corners with a corner radius of 0.2 mm may gradually increase from the position of 0.2 mm before second flow path end part 14A. In this case, the cross-sectional area of the flow path increases three times. In cases where the amount of solution is approximately 5 µL, the width of the second chamber is preferably between 1 mm and 5 mm. Therefore, when the structure of the flow path is as described above, the rate of increase of the cross-sectional area of the flow path is 25 times or less.

Another example is that, when the depth and width of first flow path 9A except for the vicinity of second flow path end part 14A are 0.04 mm and 0.2 mm, respectively, the depth and width of second flow path end part 14A can be 0.04 mm (unchanged) and 2 mm, respectively. To be more specific, the cross-sectional area may gradually increase from the position of 1 mm back from second flow path end part 14A with the curvature, such that concave arcs of the flow path contact the chamber. In this case, the cross-sectional area of the flow path increases ten times.

By controlling the shape of flow paths adequately, it is possible to carry out stepwise liquid transfer smoothly and reliably. In particular, in cases where a solution to be transferred is a biological sample, the solution has sometimes difficulty flowing in micro-flow paths. For example, blood plasma, which is one biological sample, is viscous compared to an electrolyte aqueous solution. And therefore blood plasma has difficulty flowing in micro-flow paths. Further, blood plasma, which is a solution containing a variety of proteins, allows the adhesive proteins to easily adhere to the interior walls of micro-flow paths, and may cause the micro-flow paths to be clogged. In particular, in cases where the micro-flow paths are approximately 60 μm or less, transfer of biological samples may be difficult.

The flow paths in the substrate of Embodiment 4 has the cross-sectional area near the outlet end parts increasing closer to the outlets. Therefore, the resistance of a solution due to viscosity is reduced, and blockage of flow paths due to adhesion of proteins little occurs. It is possible to transfer a biological sample solution with stable and good repeatability, and to realize stepwise liquid transfer even in the substrate in which micro-flow paths having a length between 4 μm and 60 μm.

Certainly, the inlet end parts of the flow paths in the substrate 2 of Embodiment 4 are the same as in the substrate in Embodiment 1, so that it is possible to realize stepwise liquid transfer.

Embodiment 5

Figures 16A, 16B:
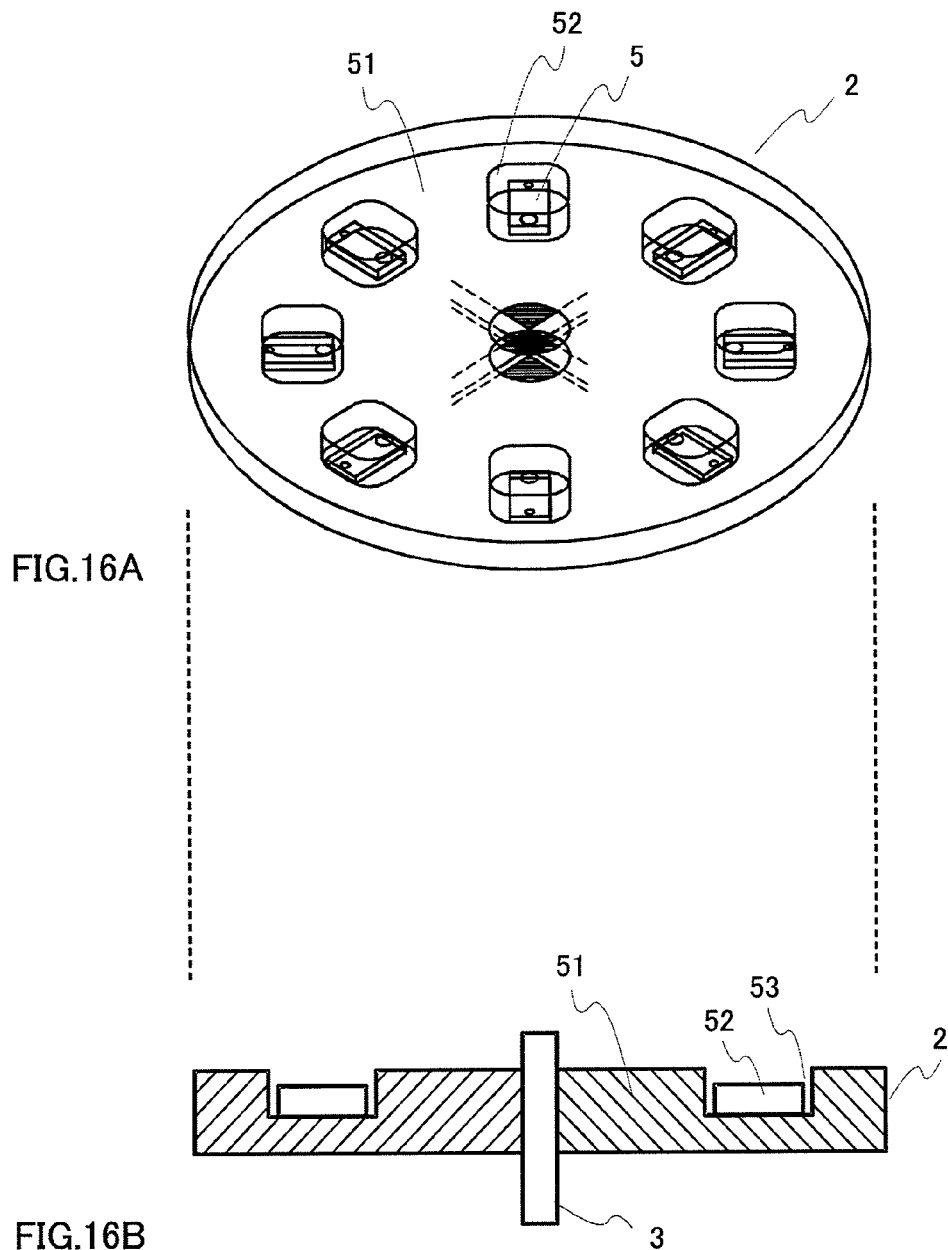
FIG. 16 is a schematic diagram showing the substrate according to Embodiment 5.

Liquid transfer apparatus 1 according to Embodiment 5 includes the rotation drive apparatus shown in FIG. 1 and substrate shown in FIGS. 16A and 16B. Substrate 2 according to Embodiment 5 has: rotating substrate body 51; and chips 52, which are removable from rotating substrate body 51. Flow path parts 5 are each formed in chips 52, not in rotating substrate body 51.

Accommodating holes 53 for accommodating chips 52 are formed on the upper face of rotating substrate body 51. A plurality of accommodating holes 53 are arranged radially with respect to rotating shaft 3. Chips 52 are arranged and supported in accommodating holes 53. Particularly, chips 52 are urged by centrifugal force when substrate 2 rotates, so that chips 52 are sure to be held in rotating substrate body 51, to prevent chips 52 from falling from accommodating holes 53.

Examples

Hereinafter, the present invention will be described more specifically with reference to the following examples. These examples do not limit the present invention.

Example 1

Example 1 corresponds to Embodiment 1. As Example 1, substrate 2 having flow path part 5 shown in FIGS. 2 to 4 (particularly FIG. 2), was made.

Design of substrate 2

Figure 17:
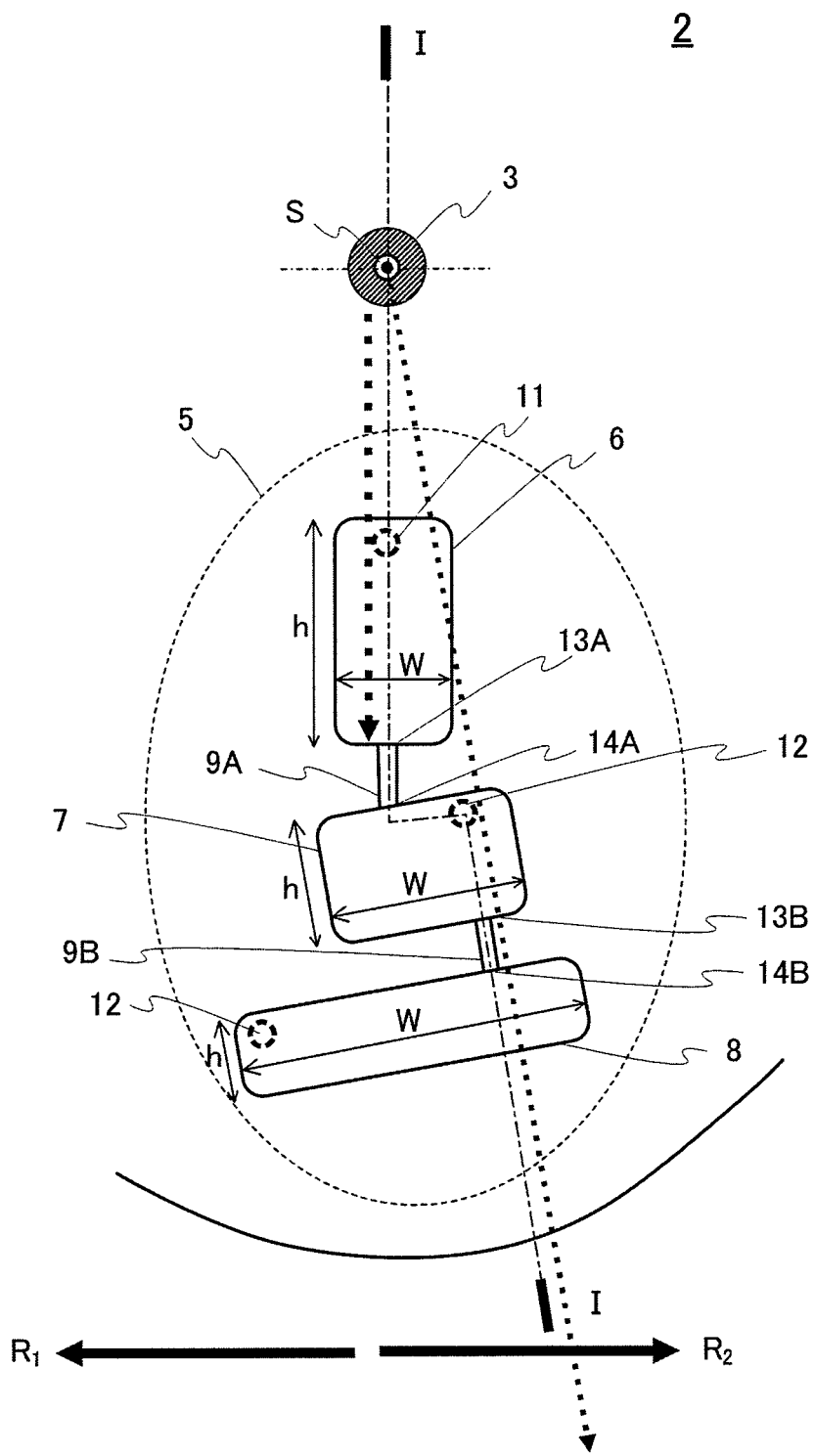
FIG. 17 is a plan view of the substrate to explain the flow path part of the substrate of Examples.

Flow path part 5 in substrate 2 shown in FIG. 17 was designed to fulfill equation 9 or 10. The design values are shown in Table 1. Meanwhile, as Comparison Example 1, substrate 2 was also designed with the design values shown in table 2.

TABLE 1

|  | Rotation Radius r (mm) | Width w (mm) | Height h (mm) | Depth d (mm) |
|---|---|---|---|---|
| 1st Chamber 6 #1 | 25 | 3 | 7 | 1 |

TABLE 1-continued

|  | Rotation Radius r (mm) | Width w (mm) | Height h (mm) | Depth d (mm) |
|---|---|---|---|---|
| 2nd Chamber 7 #2 | 35 | 9 | 3 | 1 |
| 3rd Chamber 8 #3 | 45 | 15 | 2 | 1 |
| Flow Path #c | — | 0.2 | — | 0.02 |

TABLE 2

|  | Rotation Radius r (mm) | Width w (mm) | Height h (mm) | Depth d (mm) |
|---|---|---|---|---|
| 1st Chamber 6 #1 | 25 | 5.5 | 4 | 1 |
| 2nd Chamber 7 #2 | 35 | 5.5 | 4 | 1 |
| 3rd Chamber 8 #3 | 45 | 5.5 | 4 | 1 |
| Flow Path #c | — | 0.2 | — | 0.02 |

Figure 18:
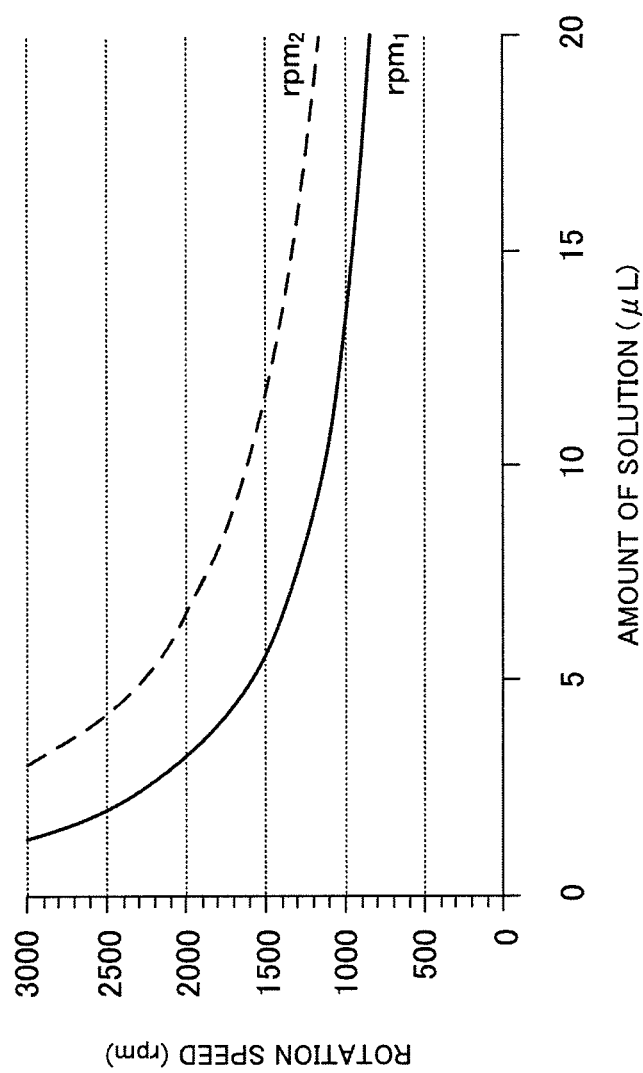
FIG. 18 is a chart showing the calculation results of the amount of solution to transfer and the speed of rotation at which liquid transfer starts from the chambers, in the substrate of Example 1.

FIG. 18 shows the calculation results of the possible first rotation speed $rpm_1$ and the possible second rotation speed $rpm_2$ with respect to substrate 2 of Example 1. The first rotation speed $rpm_1$ refers to the minimum rotation speed at which solution was transferred from first chamber 6 to second chamber 7. The second rotation speed $rpm_2$ refers to the minimum rotation speed at which solution was transferred from second chamber 7 to third chamber 8. As shown in FIG. 18, it is found out that the first rotation speed is lower than the second rotation speed. Therefore, it is evident that solution is transferred from first chamber 6 to second chamber 7 at the first rotation speed, and retained in second chamber 7 on a temporary basis; after that, the solution is transferred from second chamber 7 to third chamber 8 at the second rotation speed.

Figure 19:
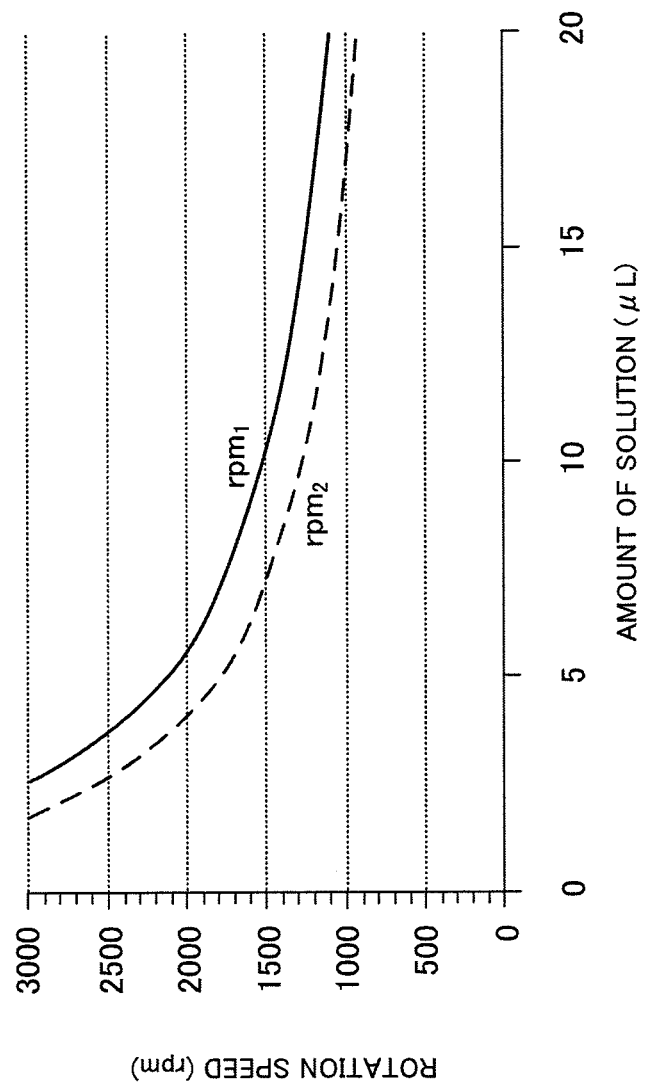
FIG. 19 is a chart showing the calculation results of the amount of solution to transfer and the speed of rotation at which liquid transfer starts from the chambers, in the substrate of Comparison Example 1.

Meanwhile, FIG. 19 shows the calculation results of the possible first rotation speed $rpm_1$ and the possible second rotation speed $rpm_2$ in substrate 2 of Comparison Example 1. As shown in FIG. 19, the first rotation speed is higher than the second rotation speed. Therefore, it is evident that, when a solution is transferred from the first chamber to second chamber 7 at the first rotation speed, the solution flows in third chamber 8 without staying in second chamber 7.

Production of substrate 2

Substrate 2 of Example 1 was made based on the design values of Table 1 and substrate 2 of Comparison Example 1 was made based on the design values of Table 2. The behavior of stepwise liquid transfer was confirmed.

A negative thick film photoresist KMPR1030 (Nippon Kayaku Co., Ltd) was applied to a glass sheet treated clean. The KMPR 1030 is spin-coated with spincoater: pre-rotated ten seconds at 500 rpm, followed by thirty seconds of main rotation at 1000 rpm. By changing the rotation speed of main rotation, it was possible to change the thickness of the film. After that, pre-bake was carried out for 20 minutes at 95C.°, and exposure was made via a mask on which flow paths and chambers were drawn. The intensity of exposure was approximately 1700 mJ/cm². PEB (Post Exposure Bake) was performed for 6 minutes at 95C.° and development was carried out, to form flow paths and chamber patterns by photolithography. Further, the chamber parts in lower part plate material 50 were formed by cutting.

Finally, flow path plate material 49, in which injection inlet 11 and air opening 12 were open, was stacked over lower part plate material 50.

Stepwise Liquid Transfer Test

As a sample solution, pure water or pure water mixed with blue pigments for improved visibility was used. A sample solution of 15 μL was injected in first chamber 6 with a pipette through injection inlet 11 in substrate 2 of Example 1. After that, when substrate 2 was mounted on liquid transfer apparatus 1 and driven in rotation at a rotation speed 892 rpm, transfer of the sample solution from first chamber 6 to second chamber 7 was observed. The sample solution did not flow in third chamber 8 and stayed in second chamber 7. After that, when the rotation speed was increased up to 1383 rpm, transfer of the sample solution from second chamber 7 to third chamber 8 was observed.

Similar test was conducted for substrate 2 of Comparison Example 1. As a result, solution 10 in first chamber 6 did not flow in flow path 9A up to a rotation speed 1400 rpm. And the solution having flown in flow path 9A passed through the second chamber and flowed in third chamber 8 at the same rotation speed.

In this way, stepwise liquid transfer was confirmed by the experiment in Example. Further, the calculated theoretical values and the rotation speed observed in the experiments matched.

Example 2

Figure 20:
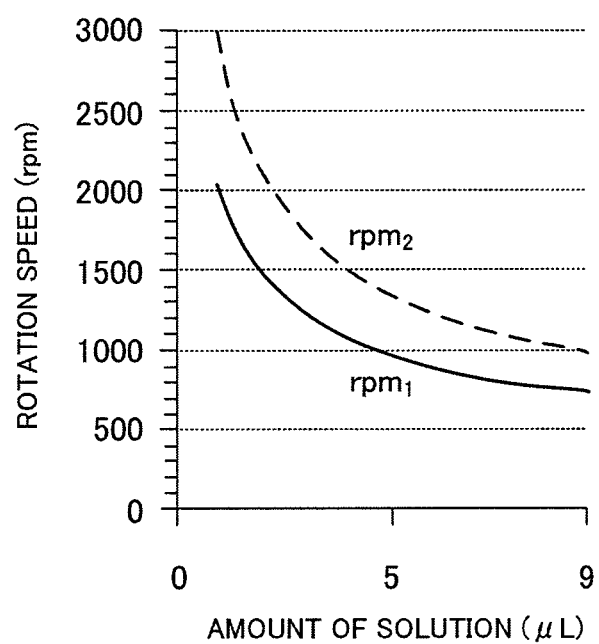
FIG. 20 is a chart showing the calculation results of the amount of solution to transfer and the speed of rotation at which liquid transfer starts from the chambers, in the substrate of Example 2.

Example 2 corresponds to Embodiment 2. Example 2 differs from Example 1 in changing the depth of chambers, not the width of chambers. The designing method, the production method and the steps of stepwise liquid transfer for substrate 2 will be the same as in Example 1, and therefore will be omitted. The design values of substrate 2 of Example 2 are shown in Table 3. FIG. 20 shows the calculation results of the first rotation speed and second rotation speed.

TABLE 3

|  | Rotation Radius r (mm) | Width w (mm) | Height h (mm) | Depth d (mm) |
|---|---|---|---|---|
| 1st Chamber 6 #1 | 25 | 5 | 10 | 0.2 |
| 2nd Chamber 7 #2 | 35 | 5 | 3 | 0.6 |
| 3rd Chamber 8 #3 | 45 | 15 | 2 | 1 |
| Flow Path #c | — | 0.2 | — | 0.02 |

Figure 21:
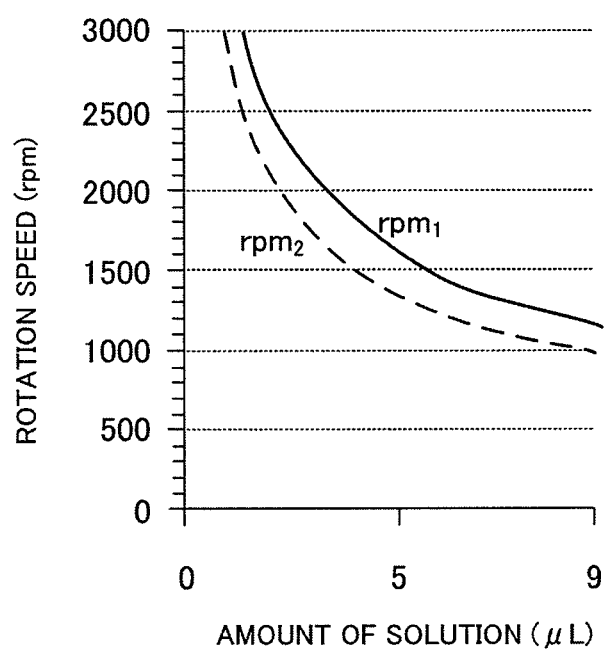
FIG. 21 is a chart showing the calculation results of the amount of solution to transfer and the speed of rotation at which liquid transfer starts from the chambers, in the substrate of Comparison Example 2.

Meanwhile, Table 4 shows the design values of substrate 2 without changing the depth of chambers, as Comparison Example 2. FIG. 21 shows the calculation results of the first rotation speed and the second rotation speed.

TABLE 4

|  | Rotation Radius r (mm) | Width w (mm) | Height h (mm) | Depth d (mm) |
|---|---|---|---|---|
| 1st Chamber 6 #1 | 25 | 5 | 10 | 0.6 |
| 2nd Chamber 7 #2 | 35 | 5 | 3 | 0.6 |

TABLE 4-continued

|  | Rotation Radius r (mm) | Width w (mm) | Height h (mm) | Depth d (mm) |
|---|---|---|---|---|
| 3rd Chamber 8 #3 | 45 | 15 | 2 | 1 |
| Flow Path #c | — | 0.2 | — | 0.02 |

Also in substrate 2 of Example 2, the first rotation speed $rpm_1$ was lower than the second rotation speed $rpm_2$, so that it was confirmed that stepwise liquid transfer was realized. Further, substrate 2 of Example 2 was made and stepwise liquid transfer was confirmed by the experiment. A sample solution of 5 μL was injected in first chamber 6 with a pipette through injection inlet 11 in substrate 2 of Example 2. After that, when substrate 2 was mounted on liquid transfer apparatus 1 and driven in rotation at a rotation speed 960 rpm, transfer of the sample solution from first chamber 6 to second chamber 7 was observed. The sample solution did not flow in third chamber 8 and stayed in second chamber 7. After that, when the rotation speed was increased up to 1448 rpm, transfer of the sample solution from second chamber 7 to third chamber 8 was observed.

Similar test was conducted for substrate 2 of Comparison Example 2. As a result, solution 10 in first chamber 6 did not flow in flow path 9A up to a rotation speed 1890 rpm. And the solution having flown in flow path 9A passed through the second chamber to flow in third chamber 8 at the same rotation speed.

In this way, stepwise liquid transfer was confirmed by the experiment in Example. Further, the calculated theoretical values and the rotation speed observed in the experiments matched.

Example 3

Figure 22:
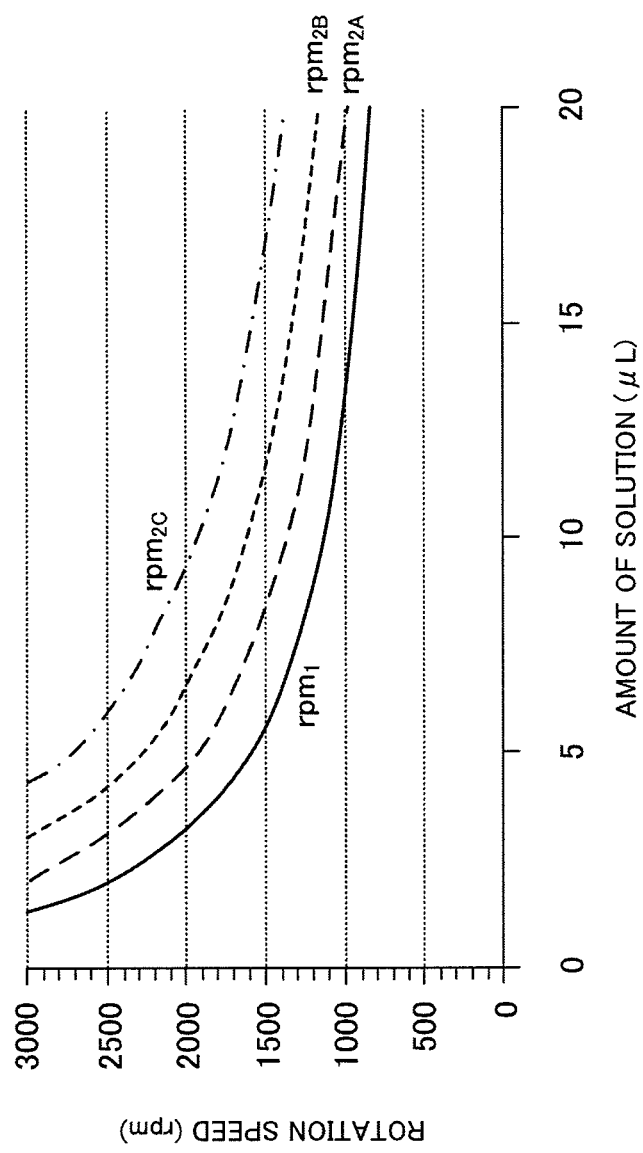
FIG. 22 is a chart showing the calculation results of the amount of solution to transfer and the speed of rotation at which liquid transfer starts from the chambers, in the substrate of Example 3.

Example 3 corresponds to Embodiment 3. Example 3 differs from Example 1 in the number of stages of chambers. Since the designing method, the production method and the step of stepwise liquid transfer of substrate 2 will be the same as in Example 1, and therefore the description will be omitted. The design values of substrate 2 are shown in Table 5. Flow path part 5 having chambers used in five stages was designed. FIG. 22 shows the calculation results of the first rotation speed $rpm_1$, second rotation speed $rpm_{2A}$, second rotation speed $rpm_{2B}$, and second rotation speed $rpm_{2C}$. The relationship $rpm_1 < rpm_{2A} < rpm_{2B} < rpm_{2C}$ was fulfilled, so that it was confirmed that stepwise liquid transfer was realized. Further, substrate 2 was made and stepwise liquid transfer was confirmed by the experiment.

A sample solution of 15 μL was injected in first chamber 6 with a pipette through injection inlet 11 in substrate 2 of Example 3. After that, when substrate 2 was mounted on liquid transfer apparatus 1 and driven in rotation at a rotation speed 888 rpm, transfer of the sample solution from first chamber 6 to second chamber 7A was observed. The sample solution did not flow in second chamber 7B and stayed in second chamber 7A. When the rotation speed was increased up to 1180 rpm after the rotation was maintained at 888 rpm in fifteen seconds, transfer of the sample solution from second chamber 7B to second chamber 7C was observed. When the rotation speed was increased up to 1347 rpm in thirty seconds from the start of rotation drive after the rotation was maintained at 1180 rpm in fifteen seconds, transfer of the sample solution from second chamber 7B to second chamber 7C was observed. All the solution in second chamber 7B was transferred to second chamber 7C four seconds after the start of liquid transfer (i.e. thirty four seconds after the start of rotation drive). After that, when the rotation speed was increased up to 1635 rpm after seventy-five seconds from the start of rotation, transfer of the sample solution from second chamber 7C to third chamber 8 was observed. All the solution in second chamber 7C was transferred to third chamber 8 three seconds after the start of liquid transfer (i.e. seventy-eight seconds after the start of rotation drive).

In this way, the stepwise liquid transfer using four stages was confirmed by the experiment in Example. Further, the calculated theoretical values and the rotation speed observed in the experiment matched with respect to $rpm_1$, $rpm_{2A}$, and $rpm_{2B}$. With regards to $rpm_{2C}$, the theoretical value was less than the values by the experiment. Although the imaginary chamber length of second chamber 7C was theoretically 1 mm in a width of 15 mm, the actual imaginary chamber length was 1.2 mm. Second chamber 7C has hydrophobic inner wall surface and formed in laterally long, therefore the solution surface in second chamber 7C is subjected to surface tension and seemed to be curved in a plan view. As a result, the actual imaginary chamber length was 1.2 mm. The rotation speed $rpm_1$ and $rpm_{2B}$ in the experiment in Example 1 was repeated.

TABLE 5

| | Rotation Radius r (mm) | Width w (mm) | Height h (mm) | Depth d (mm) |
|---|---|---|---|---|
| 1st Chamber 6 #1 | 25 | 3 | 7 | 1 |
| 2nd Chamber 7A #2 | 30 | 5.5 | 4 | 1 |
| 2nd Chamber 7B #3 | 35 | 9 | 3 | 1 |
| 2nd Chamber 7C #4 | 40 | 15 | 1.5 | 1 |
| 3rd Chamber 8 #5 | 45 | 18 | 2 | 1 |
| Flow Path #c | — | 0.2 | — | 0.02 |

Example 4

Example 4 corresponds to Embodiment 4. This example differs from Example 1 in changing (expanding) the width of outlet end parts of both the first flow path and the second flow path. To be more specific, the flow paths have a width of 0.6 mm at outlet end parts and a width of 0.2 mm at the center part other than the end parts. As shown in FIG. 15, the width of the flow paths gradually expands and becomes 0.6 mm such that the flow paths have round corners with a corner radius of 0.2 mm from the position of 0.2 mm before the outlet end parts. The depth of flow paths in Example 4 and the following Comparison Examples 4A to 4C was 0.04 mm and did not change in the outlet end parts or in the inlet end parts.

Meanwhile, in Comparison Example 4A, as in Example 1, the width of flow paths near the inlet end parts and the outlet end parts was 0.2 mm, and stayed constant. In Comparison Example 4B, the width of flow paths near the outlet end parts was 0.2 mm and constant, and the width of flow paths near the inlet end parts was changed (contracted). In a plan view, the contracted shape is opposite plane to the present example. Specifically, the first flow path and the second flow path have a width of 0.2 mm except for inlet end parts, and the width of inlet end parts is 0.6 mm. In a plan view, the width of the flow paths gradually contract such that the flow paths have round corners with a corner radius of 0.2 mm, from the position of 0.2 mm rear side of inlet end parts of the flow paths. In Comparison Example 4C, the shapes near the outlet end parts and near the inlet end parts change.

Table 6 shows the results of stepwise liquid transfer tests using human blood plasma reagents on the day of the test. In the tests, human blood plasma of 5 μL was injected in first chamber to conduct three to nine repeated tests. The table shows the rate between the number of times the test was conducted and the number of times a blood plasma reagent succeeded in being transferred stepwise. The rate of successful liquid transfer in substrate 2 having the flow path end parts shown in Comparison Example 4A to 4C was 40% or less. On the other hand, the rate of successful liquid transfer in substrate 2 of Example 4 was 100%, so that it results in reliably transferring human blood plasma reagents stepwise.

TABLE 6

| | | Flow Path Inlet end part | |
|---|---|---|---|
| | | Fixed Width of flow paths | Contracted Width of flow paths |
| Flow Path Outlet End Part | Fixed Width of flow paths | Comparison Example 4A 33% (1/3) | Comparison Example 4B 22% (2/9) |
| | Expanded Width of flow paths | Comparison Example 4 100% (3/3) | Comparison Example 4C 40% (2/5) |

The steps of liquid transfer test included, first, rotating the substrate from rotation speed 1200 rpm, and, after thirty seconds have passed, the rotation speed was increased 10 rpm every second, up to 3500 rpm that was the limit of the motor.

The rate of successful liquid transfer in substrate 2 of Comparison Example 4A was one time in three times (33%). In the one successful time, although a solution was transferred from first chamber 6 to second chamber 7 at a rotation speed 2051 rpm, the solution was not transferred from second chamber 7 to third chamber 8 until the rotation speed reached 3500 rpm. The rate of successful liquid transfer in substrate 2 of Comparison Example 4B was two times in nine times (22%). In the two successful times, although a solution was transferred from first chamber 6 to second chamber 7 at a rotation speed 1542 rpm (the average of the two tests), and the rotation speed at the start was not uniform and the C.V. (coefficient of variation) was 4.2%. After that, a solution was not transferred from second chamber 7 to third chamber 8 until the rotation speed reached 3500 rpm. The rate of successful liquid transfer in substrate 2 of Comparison Example 4C was two times in five times (40%). In the two successful times, although a solution was transferred from first chamber 6 to second chamber 7 at a rotation speed 2160 rpm (the average of the two tests), and the rotation speed at the start was not uniform and the C.V. (coefficient of variation) was 5.8%. After that, the solution was not transferred from second chamber 7 to third chamber 8 until the rotation speed reached 3500 rpm.

The successful rate of liquid transfer in substrate 2 of Example 4 was three times in three times (100%). A solution was transferred from first chamber 6 to second chamber 7 at a rotation speed 1512 rpm (the average of the three times), and the rotation speed at the start little is uniform and the C.V. (coefficient of variation) was 0.5%, compared with Comparison Examples 4A to 4C. The solution was transferred from second chamber 7 to third chamber 8 at the rotation speed 1950 rpm (an average of three times). The C.V was as stable as 0.5%.

As described above, as a result, substrate 2 of Example 4 was able to not only transfer a human blood plasma reagent stepwise reliably, and the rotation speed at the start of rotation was always constant.

The disclosure of Japanese Patent Application No. 2007-125908, filed on May 10, 2007, including the specification, drawings and abstract, is incorporated herein by reference in its entirety.

INDUSTRIAL APPLICABILITY

The substrate and method for transferring solution according to the present invention are suitable for use as driving sources for a device for analyzing components produced by a living organism such as biological samples and, in particular, proteins included in blood. Particularly, proteins contained in blood plasma, which are obtained by separating the blood cells from blood plasma in a preparatory stage, are targeted as a measurement sample. Further, centrifugal separation, which uses centrifugal force, is suitable for use in the separation. For that reason, a method of liquid transfer using a substrate can be combined easily with separation of the blood cells from blood plasma using centrifugal force. Further, by carrying reagents in chambers and conducting physical operation such as heating on chambers, it is possible to carry out reaction, purification and detection. For this reason, the present invention is applicable for use in POCT (Point of care test) biosensors that separate, purify, react and detect proteins and materials that serve as an indicator of health contained in a blood sample.

EXPLANATION OF REFERENCE NUMERALS

1 LIQUID TRANSFER APPARATUS
2 ROTATING SUBSTRATE
3 ROTATING SHAFT
4 ROTATION DRIVE PART
5 FLOW PATH PART
6 FIRST CHAMBER (SUPPLY SOURCE CHAMBER)
7, 7A and 7B SECOND CHAMBER (SUPPLY DESTINATION CHAMBER)
8 THIRD CHAMBER (FINAL STAGE CHAMBER)
9A, 9B, and 9C FLOW PATH
10 SOLUTION (or BIOLOGICAL SAMPLE SOLUTION)
11 INJECTION INLET
12 AIR OPENING
13A FIRST FLOW PATH END PART (INLET END PART)
13B THIRD FLOW PATH END PART (INLET END PART)
13C FIFTH FLOW PATH END PART (INLET END PART)
14A SECOND FLOW PATH END PART (OUTLET END PART)
14A FOURTH FLOW PATH END PART (OUTLET END PART)
14C SIXTH FLOW PATH END PART (OUTLET END PART)
21 FIRST CHAMBER WIDTH
22 SECOND CHAMBER WIDTH
23 THIRD CHAMBER WIDTH
24 FIRST CHAMBER DEPTH
25 SECOND CHAMBER DEPTH
26 THIRD CHAMBER DEPTH
27A, 27B, and 27C FLOW PATH DEPTH
31 MOTOR
32 DRIVING CIRCUIT
33 CONTROL SIGNAL OUTPUT SECTION
34 SPEED CHARACTERISTIC APPLICATION SECTION
35 ROTATION SPEED DETECTOR
36 ROTATION SPEED CONTROL SECTION
41 UPPER PLATE MATERIAL
42 FLOW PATH PLATE MATERIAL
43 CHAMBER PLATE MATERIAL
44 LOWER PLATE MATERIAL
46 and 47 GROOVE HOLE
48 CAVITY
49 FLOW PATH PLATE MATERIAL
50 LOWER PART PLATE MATERIAL
51 ROTATING SUBSTRATE BODY
52 CHIP
53 ACCOMMODATING HOLE
$Y_1$ FIRST IMAGINARY CHAMBER LENGTH
$Y_2$ SECOND IMAGINARY CHAMBER LENGTH
$R_1$ CLOCKWISE DIRECTION
$R_2$ COUNTERCLOCKWISE DIRECTION
S AXIS OF ROTATION (AXIS)
r RADIAL DIRECTION
$r_{1d}$ RADIUS OF ROTATION OF FIRST CHAMBER
$r_{1u}$ ROTATION RADIUS OF IMAGINARY LIQUID SURFACE IN FIRST CHAMBER
$r_{2d}$ RADIUS OF ROTATION IN SECOND CHAMBER
$r_{2u}$ ROTATION RADIUS OF IMAGINARY LIQUID SURFACE IN SECOND CHAMBER
$Fc_1$ FIRST CAPILLARY FORCE
$Fc_{2A}$ and $Fc_{2B}$ FIRST CAPILLARY FORCE
$Pc_1$ FIRST CAPILLARY PRESSURE
$Pc_{2A}$ and $Pc_{2B}$ SECOND CAPILLARY PRESSURE
$Fg_1$ FIRST CENTRIFUGAL FORCE
$Fg_{2A}$ and $Fg_{2B}$ SECOND CENTRIFUGAL FORCE
$Pg_1$ FIRST CENTRIFUGAL PRESSURE
$Pg_{2A}$ and $Pg_{2B}$ SECOND CENTRIFUGAL PRESSURE
$T_1$ to $T_n$ SURFACE TENSIONS
$\theta c_1$ FIRST CONTACT ANGLE
$\theta c_2$ SECOND CONTACT ANGLE
$V_1$ FIRST CONTRIBUTION VOLUME
$V_2$ SECOND CONTRIBUTION VOLUME
dv MICRO VOLUME
dp MICRO-CENTRIFUGAL PRESSURE

The invention claimed is:

1. A substrate that is rotatable around an axis of rotation and that has a flow path part formed inside the substrate, wherein the flow path part comprises:
(A) a first chamber that has an injection inlet;
(B) a second chamber that is shorter in length and greater in width than the first chamber and that is placed in a position more distant from the axis of rotation than the first chamber;
(C) a third chamber that is shorter in length and greater in width than the second chamber, that is connected with outer atmosphere of the substrate via an air opening, and that is placed in a position more distant from the axis of rotation than the second chamber;
(D) a first flow path that communicates the first chamber and the second chamber, that has a first flow path end part connected with the first chamber and is placed in a position more distant from the axis of rotation than the injection inlet, and that has a second flow path end part connected with the second chamber;
(E) a second flow path that communicates the second chamber and the third chamber, that has a third flow path end part connected with the second chamber and is not placed on a straight line connecting the axis of rotation and the second flow path end part, and that has a fourth flow path end part connected with the third chamber and placed in a position more distant from the axis of rotation than the second flow path end part; such that a solution to be provided in the substrate is transferred stepwise in order of the first chamber, second chamber and third chamber;

a cross-sectional area of a bottom surface of the first chamber near the first flow path end part is larger than the cross-sectional area of the first flow path near the first flow path end part;

the cross-sectional area of the third flow path end part is the same or larger than the cross-sectional area of the first flow path end part, and a width of the first chamber near the first flow path end part is narrower than the width of the second chamber near the third flow path end part, or a depth of the first chamber near the first flow path end part is shallower than the depth of the second chamber near the third flow path end part, wherein an imaginary length of the first chamber is longer than an imaginary length of the second chamber, the imaginary length of the first chamber is defined as the distance from the first flow path end part to a surface of the solution along the centripetal direction toward the axis of rotation, when all of an amount of the solution is accommodated in the first chamber and the substrate rotates about the axis of rotation so as to force all of the amount of the solution in a direction in which centrifugal force acts in a state that all of the amount of the solution is retained in the first chamber, and the imaginary length of the second chamber is defined as the distance from the third flow path end part to a surface of the solution along the centripetal direction toward the axis of rotation, when all of the amount of the solution is accommodated in the second chamber and the substrate rotates about the axis of rotation so as to force all of the amount of the solution in a direction in which centrifugal force acts in a state that all of the amount of the solution is retained in the second chamber.

2. The substrate according to claim 1, wherein:

the width of the first flow path except for the first flow path end part and the second flow path end part, and the width of the second flow path except for the third flow path end part and the fourth flow path end part, are 4 micrometers or more and less than 60 micrometers;

the cross-sectional area of the first flow path near the first flow path end part, and the cross-sectional area of the second flow path near the third flow path end part, are constant or increase in the centrifugal direction; and the cross-sectional area of the first flow path near the second flow path end part, and the cross-sectional area of the second flow path near the fourth flow path end part, increase in the centrifugal direction.

3. The substrate according to claim 1, wherein:

the depth of the first flow path except for the first flow path end part and the second flow path end part, and the depth of the second flow path except for the third flow path end part and the fourth flow path end part, are 4 micrometers or more and less than 60 micrometers;

the cross-sectional area of the first flow path near the first flow path end part, and the cross-sectional area of the second flow path near the third flow path end part, are constant or increase in the centrifugal direction; and the cross-sectional area of the first flow path near the second flow path end part, and the cross-sectional area of the second flow path near the fourth flow path end part, increase in the centrifugal direction.

4. The substrate according to claim 1, wherein the second chamber has an air opening, and is spatially closed except for the air opening.

5. The substrate according to claim 1, wherein the flow path part further comprises:

two or more second chambers of a second chamber A and a second chamber B, the second chamber A being placed nearer the axis of rotation than the second chamber B; and a third flow path that communicates the second chamber A and the second chamber B formed in the substrate, that has a fifth flow path end part, which is connected with the second chamber A in a position more distant from the axis of rotation than the second flow path end part, and which is not placed on a straight line connecting the axis of rotation and the second flow path end part, and that has a sixth flow path end part connected with the second chamber B; and a width of the second chamber A near the first flow path end part is narrower than the width of the second chamber B near the third flow path end part, or a depth of the second chamber A near the first flow path end part is shallower than the depth of the second chamber B near the third flow path end part such that an imaginary length of second chamber A is longer than an imaginary length of second chamber B, the imaginary length of second chamber A is defined as the distance from the fifth flow path end part to a surface of the solution along the centripetal direction toward the axis of rotation, when all of the amount of the solution is accommodated in the second chamber A and the substrate rotates about the axis of rotation so as to force all of the amount of the solution in a direction in which centrifugal force acts in a state that all of the amount of the solution is retained in the second chamber A, the imaginary length of second chamber B is defined as the distance from the third flow path end part to a surface of the solution along the centripetal direction toward the axis of rotation, when all of the amount of the solution is accommodated in the second chamber B and the substrate rotates about the axis of rotation so as to force all of the amount of the solution in a direction in which centrifugal force acts in a state that all of the amount of the solution is retained in the second chamber B.

6. The substrate according to claim 1, comprising:

two or more of the flow path parts.

7. The substrate according to claim 6, further comprising:

a rotating shaft that works as the axis of rotation.

8. The substrate according to claim 1, wherein the first flow path end part and the third flow path end part are hydrophobic.

9. The substrate according to claim 5, wherein the first flow path end part, the third flow path end part and the fifth flow path end part are hydrophobic.

10. The substrate according to claim 1, wherein the first flow path and the second flow path are entirely hydrophobic.

11. The substrate according to claim 5, wherein the first flow path, the second flow path and the third flow path are entirely hydrophobic.

12. The substrate according to claim 1, wherein the flow path part is entirely hydrophobic.

13. A multistage liquid transfer method, comprising:

preparing the substrate according to claim 1, in which a solution is accommodated in the first chamber;

rotating the substrate around an axis of rotation at a first rotation speed $rpm_1$; and rotating the substrate at a second rotation speed $rpm_2$ higher than the first rotation speed $rpm_1$.

14. A multistage liquid transfer apparatus, comprising:

the substrate according to claim 1; and a rotation drive part that rotates the substrate around an axis of rotation.

15. The multistage liquid transfer apparatus according to claim 14, wherein the rotation drive part comprises:

a motor that rotates the substrate around the axis of rotation; and a speed characteristic application section that gives speed characteristics to the motor.

16. The multistage liquid transfer apparatus according to claim 15, wherein the rotation drive part further comprises:

a rotation speed detector that detects the rotation speed of the substrate during rotation; and a rotation speed correction section that corrects the speed characteristics given to the motor by the speed characteristic application section based on the rotation speed detected in the rotation speed detector.

* * * * *